(12) United States Patent
Cheng et al.

(10) Patent No.: US 7,786,097 B2
(45) Date of Patent: *Aug. 31, 2010

(54) TRICYCLIC COMPOUNDS, COMPOSITIONS AND METHODS

(75) Inventors: Hengmiao (Henry) Cheng, San Diego, CA (US); Rajesh Devraj, Chesterfield, MO (US); Gary A Decresenzo, St. Charles, MO (US); Xiao Hu, St. Charles, MO (US); Kevin D. Jerome, St. Charles, MO (US); Mark Obukowicz, Kirkwood, MO (US); Lisa Olson, Hopkinton, MA (US); Paul V. Rucker, Carlsbad, CA (US); Ronald Keith Webber, St. Peters, MO (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/506,825

(22) Filed: Jul. 21, 2009

(65) Prior Publication Data

US 2009/0281148 A1  Nov. 12, 2009

Related U.S. Application Data

(63) Continuation of application No. 12/023,362, filed on Jan. 31, 2008, now Pat. No. 7,598,231.

(60) Provisional application No. 60/887,981, filed on Feb. 2, 2007.

(51) Int. Cl.
*A61K 31/675* (2006.01)
*A61K 31/44* (2006.01)

(52) U.S. Cl. .......................... 514/89; 514/352; 514/886
(58) Field of Classification Search .................. 514/89, 514/352, 886
See application file for complete search history.

(56) References Cited

U.S. PATENT DOCUMENTS

| | | | |
|---|---|---|---|
| 6,106,864 A | 8/2000 | Dolan et al. | |
| 6,380,223 B1 | 4/2002 | Dow et al. | |
| 7,138,406 B2 | 11/2006 | Chantigny et al. | |
| 7,547,714 B2 * | 6/2009 | Cheng | 514/352 |
| 7,598,231 B2 * | 10/2009 | Cheng et al. | 514/89 |
| 2002/0107235 A1 | 8/2002 | Liu et al. | |
| 2004/0014741 A1 | 1/2004 | Liu et al. | |
| 2004/0176595 A1 | 9/2004 | Dow et al. | |
| 2006/0247264 A1 | 11/2006 | Chantigny et al. | |
| 2008/0188443 A1 | 8/2008 | Cheng et al. | |

FOREIGN PATENT DOCUMENTS

| | | |
|---|---|---|
| EP | 0 188 396 | 7/1986 |
| EP | 1 201 649 | 5/2001 |
| EP | 1 201 655 | 5/2002 |
| WO | WO 98/31702 | 11/2000 |
| WO | WO01/05229 | 1/2001 |
| WO | WO03/000226 | 1/2003 |
| WO | WO03/020216 | 3/2003 |
| WO | WO03/063833 | 8/2003 |
| WO | WO00/66522 | 1/2004 |
| WO | WO2004/004653 | 1/2004 |
| WO | WO2004005229 | 1/2004 |
| WO | WO2004/041214 | 5/2004 |
| WO | WO2004/041215 | 5/2004 |
| WO | WO2004/069202 | 8/2004 |
| WO | WO2005/009382 | 2/2005 |
| WO | WO2005/009388 | 2/2005 |
| WO | WO2005/047254 | 5/2005 |
| WO | WO2007131041 | 11/2007 |

OTHER PUBLICATIONS

Adcock, et al.; 2006; New Insights into the Molecular Mechanisms of Corticosteroids Actions; Current Drug Targets; 7; 649-660.

Buttgereit, et al.; 2005; Optimised glucocorticoid therapy: the sharpening of an old spear; Lancet; 365; 801-803.

Catley; 2007; Dissociated Steroids; The Scientific World; 7; 421-430.

Chemical Abstracts; 1976; 84(19).

Finin & Morgan; 1999;Transdermal Penetration Enhancers:Applications, Limitations, and Potential; Journal of Pharmaceutical Science; 88(10); 955-958.

Liang & Chen; 2001; Fast-dissolving intraoral drug delivery systems; Expert Opinion in Therapeutic Patents; 11(6); 981-986.

(Continued)

*Primary Examiner*—Charanjit S Aulakh
(74) *Attorney, Agent, or Firm*—A. David Joran

(57) ABSTRACT

The present invention is directed to compounds of Formula I:

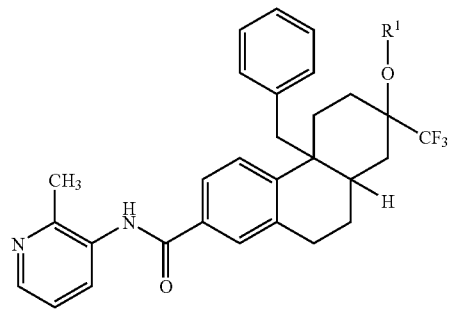

or salt thereof, which are modulators of the glucocorticoid receptor. The compounds and salts of the invention are useful in the treatment of conditions mediated by glucocorticoid receptor activity.

8 Claims, No Drawings

OTHER PUBLICATIONS

Miner, et al.;2005; New and improved glucocorticoid receptor ligands; Expert Opinion in Investigative Drugs; 14(12); 1527-1545.

Mohler, et al; 2007; Dissociated non-steroidal glucocorticoids: tuning out untoward effects; Expert Opinion on Investigative Drugs; 17(1); 37-58.

Morgan,et al.;2004;Discovery of potent, Non-Steroidal and Highly Selective Glucocorticoid Receptor Antagonists w/Anti-Obesity Activity;Letters in Drug Design & Discovery;1;1-5.

Morgan,et al.;2002;Discovery of potent, Non-Steroidal and Highly Selective Glucocorticoid Receptor Antagonists w/Anti-Obesity Activity; J. Of Med. Chem; 45;2417-2424.

Verma, et al.; 2001; Current Status of Drug Delivery Technologies and Future Directions;:Pharmaceutical Technology On-Line;25(2);1-14.

Preliminary Amendment filed Feb. 19, 2002 in U.S. Appl. No. 10/080,174.

* cited by examiner

TRICYCLIC COMPOUNDS, COMPOSITIONS AND METHODS

CROSS REFERENCE TO RELATED APPLICATIONS

This is a continuation of U.S. application Ser. No. 12/023,362, filed 31 Jan. 2008 now U.S. Pat. No. 7,598,231, which claims the benefit of U.S. provisional application Ser. No. 60/887,981, filed 2 Feb. 2007, both of which are incorporated by reference.

FIELD OF THE INVENTION

The present invention includes compounds that are glucocorticoid receptor modulators. The present invention also includes compositions and methods of using compounds and compositions.

BACKGROUND OF THE INVENTION

Glucocorticoid receptor modulators are glucocorticoid receptor ligands that are used to treat a variety of conditions because of their powerful anti-inflammatory, antiproliferative and immunomodulatory activity. J. Miner, et al., Expert Opin. Investig. Drugs (2005) 14(12):1527-1545.

Examples of glucocorticoid receptor modulators include dexamethasone, prednisone, prednisolone, RU-486, and as described in WO 2000/66522 and WO 2004/005229.

Treatment with glucocorticoid receptor modulators is often associated with side effects, such as bone loss and osteoporosis.

Identifying a glucocorticoid receptor modulator that is efficacious, potent, and has mitigated side-effects fulfills a medical need.

SUMMARY OF THE INVENTION

In one embodiment, the invention relates to a compound of Formula I:

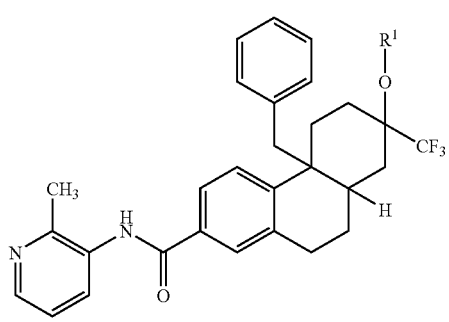

(I)

wherein $R^1$ is —H or —P(O)(OH)$_2$; or salt thereof.

In another embodiment, the invention relates to compositions comprising a compound of Formula I and a carrier. In another embodiment, the invention relates to a method of contacting a glucocorticoid receptor with a compound of Formula I. An additional embodiment includes methods of treating a condition in a subject mediated by glucocorticoid receptor activity by administering to the subject a compound of Formula I.

DETAILED DESCRIPTION

This detailed description of embodiments is intended only to acquaint others skilled in the art with the inventions, the principles, and the practical applications so that others skilled in the art may adapt and apply the inventions in their numerous forms, as they may be best suited to the requirements of a particular use. These inventions, therefore, are not limited to the embodiments described in this specification, and may be modified.

A. DEFINITIONS

For the following defined terms, these definitions shall be applied, unless a different definition is given in the claims or elsewhere in this specification.

The term "carrier" describes an ingredient other than a compound. Carriers may be pharmaceutically acceptable material or vehicle. Examples include liquid or solid filler, diluent, excipient, solvent or encapsulating material.

The phrase "contacting a glucocorticoid receptor" means in vivo, ex vivo, or in vitro contact is made with a glucocorticoid receptor and includes administration of a compound or salt of the present invention to a subject having a glucocorticoid receptor, as well as, for example, introducing a compound or salt of the invention into a sample containing a cellular, unpurified, or purified preparation containing the glucocorticoid receptor. For example, contacting includes interactions between the compound and the receptor, such as binding.

The phrase "inflammation related condition" includes arthritis, fibromyalgia, ankylosing spondylitis, psoriasis, systemic lupus erythematosus, gout, undifferentiated spondyloarthropy, juvenile-onset spondyloarthritis, Crohn's disease, ulcerative colitis, irritable bowel syndrome, inflammatory bowel disease and pain associated with the aforementioned conditions. Specific examples of arthritis include rheumatoid arthritis, osteoarthritis, reactive arthritis, infectious arthritis, psoriatic arthritis, polyarthritis, juvenile arthritis, juvenile rheumatoid arthritis, juvenile reactive arthritis, and juvenile psoriatic arthritis.

The term "modulation" or "modulators" includes antagonist, agonist, partial antagonists, and partial agonists.

The term "subject" refers to any animal, including mammals, such as mice, rats, other rodents, rabbits, dogs, cats, pigs, cattle, sheep, horses, primates, or humans.

The term "treating" (and corresponding terms "treat" and "treatment") includes palliative, restorative, and preventative ("prophylactic") treating of a subject. The term "palliative treating" refers to treatment that eases or reduces the effect or intensity of a condition in a subject without curing the condition. The term "preventative treating" (and the corresponding term "prophylactic treating") refers to treatment that prevents the occurrence of a condition in a subject. The term "restorative treating" ("curative") refers to treatment that halts the progression of, reduces the pathologic manifestations of, or entirely eliminates a condition in a subject. Treating can be done with a therapeutically effective amount of compound, salt or composition that elicits the biological or medicinal response of a tissue, system or subject that is being sought by an individual such as a researcher, doctor, veterinarian, or clinician.

B. COMPOUNDS

The present invention comprises, in part, tricyclic compounds of Formula I. These compounds are useful as glucocorticoid receptor modulators.

The present invention includes a compound of Formula I:

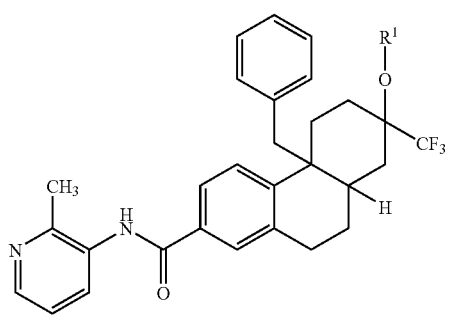

wherein $R^1$ is —H or —P(O)(OH)$_2$; or salt thereof.

The present invention includes a compound of Formula II:

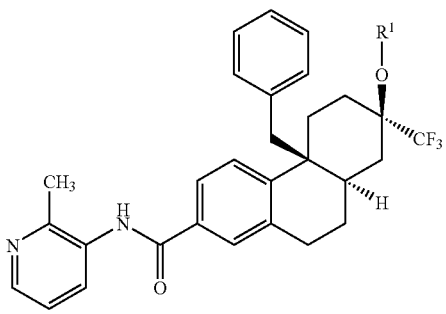

wherein $R^1$ is —H or —P(O)(OH)$_2$; or salt thereof.

The present invention includes compounds of Formula I or II wherein $R^1$ is —H, or salt thereof.

The present invention includes compounds of Formula I or II wherein $R^1$ is —P(O)(OH)$_2$, or salt thereof.

The present invention includes (4βS,7R,8αR)-4β-benzyl-7-hydroxy-N-(2-methylpyridin-3-yl)-7-(trifluoromethyl)-4β,5,6,7,8,8α,9,10-octahydrophenanthrene-2-carboxamide or salt thereof; and (2R,4αS,10αR)-4α-benzyl-7 (2-methylpyridin-3-yl)carbamoyl)-2-(trifluoromethyl)-1,2,3,4,4α,9,10,10α-octahydrophenanthren-2-yl dihydrogen phosphate or salt thereof.

Salts of compounds of the present invention include the acid addition and base salts (including disalts) thereof. In one embodiment, the present invention includes a hydrochloride salt of the compound of Formula I. In another embodiment, the present invention includes a calcium salt of the compound of Formula I. In another embodiment, the present invention includes a sodium salt of the compound of Formula I.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002).

A salt may be readily prepared by mixing together solutions of compounds of the present invention and the desired acid or base, as appropriate. The salt may precipitate from solution and be collected by filtration or may be recovered by evaporation of the solvent. The degree of ionization in the salt may vary from completely ionized to almost non-ionized.

The compounds of the present invention may be administered as prodrugs. Thus, certain derivatives which may have little or no pharmacological activity themselves can, when administered into or onto the body, be converted into compounds of the present invention having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs can, for example, be produced by replacing appropriate functionalities present in the compounds of the present invention with certain moieties known to those skilled in the art as 'pro-moieties' as described, for example, in "Design of Prodrugs" by H Bundgaard (Elsevier, 1985).

Some examples of such prodrugs include:

(i) where the compound contains an alcohol functionality (—OH), an ether thereof, for example, replacement of the hydrogen with ($C_1$-$C_6$)alkanoyloxymethyl; and (ii) where the compound contains a secondary amino functionality, an amide thereof, for example, replacement of hydrogen with ($C_1$-$C_{10}$)alkanoyl.

Finally, certain compounds of the present invention may themselves act as prodrugs of other compounds of the present invention. For example, certain compounds of Formula I or II could be viewed as a prodrug of other compounds encompassed by Formula I or II.

All isomers, such as stereoisomers, geometric (cis/trans or Z/E) isomers and tautomeric forms of the compounds or salts are included in the scope of the present invention, including compounds or salts having more than one type of isomerism, and mixtures of one or more thereof. For example, the following depicts a compound of Formula I and a tautomer.

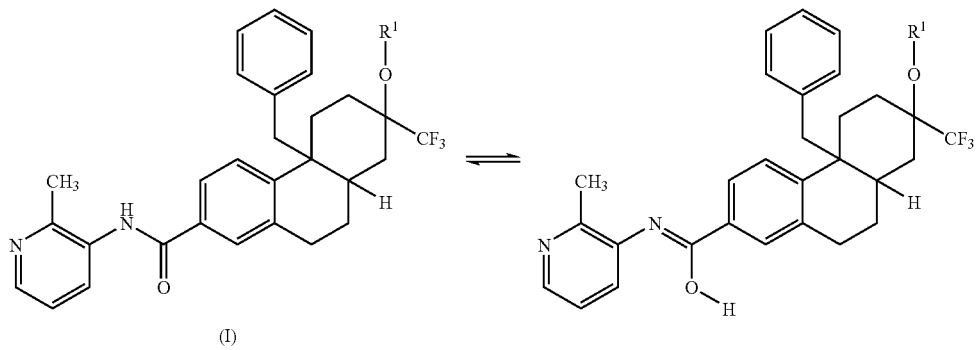

(I)

Also included are acid addition or base salts wherein the counterion is optically active, for example, D-lactate or L-lysine, or racemic, for example, DL-tartrate or DL-arginine.

Isomers may be separated by conventional techniques well known to those skilled in the art.

The present invention includes isotopically-labelled compounds of the invention wherein one or more atoms are replaced by atoms having the same atomic number, but an atomic mass or mass number different from the atomic mass or mass number usually found in nature.

Isotopically-labeled compounds of the invention can generally be prepared by conventional techniques known to those skilled in the art or by processes analogous to those described in the accompanying Examples and Preparations using an appropriate isotopically-labelled reagent in place of the non-labeled reagent previously employed.

For the treatment of the conditions referred to below, the compounds of the present invention can be administered. Salts of the compounds of the present invention could also be used.

C. COMPOSITIONS

Compounds or salts of the present invention could be part of a composition. Compositions can also include one or more compounds or salts of the present invention. The composition can also include an enantiomeric excess of one or more compounds of the present invention. Other pharmacologically active substances and carriers can be included in the composition.

One embodiment is a composition comprising a compound of Formula I or a salt thereof. Another embodiment is a composition comprising a compound of Formula I or a salt thereof and a carrier.

For example, the carrier can be an excipient. The choice of excipient will to a large extent depend on factors such as the particular mode of administration, the effect of the excipient on solubility and stability, and the nature of the dosage form.

The composition can be a solid, a liquid, or both, and may be formulated with the compound as a unit-dose composition, for example, a tablet, which can contain from 0.05% to 95% by weight of the active compounds. Compounds or salts of the present invention may be coupled with suitable polymers as targetable drug carriers.

D. METHODS

The present invention includes a method of contacting a glucocorticoid receptor with a compound or salt of the present invention.

The present invention also includes a method of treating a condition mediated by glucocorticoid receptor activity in a subject comprising administering to the subject a compound or salt of the present invention.

A condition mediated by glucocorticoid receptor activity includes:

a) endocrine disorders, such as primary or secondary adrenocortical insufficiency, congenital adrenal hyperplasia, nonsuppurative thyroiditis, and hypercalcemia associated with cancer;

b) rheumatic disorders, such as psoriatic arthritis, rheumatoid arthritis, including juvenile rheumatoid arthritis, ankylosing spondylitis, acute and subacute bursitis, acute nonspecific tenosynovitis, acute gouty arthritis, post-traumatic osteoarthritis, synovitis of osteoarthritis, and epicondylitis;

c) collagen diseases, such as systemic lupus erythematosus, and acute rheumatic carditis;

d) dermatologic conditions, such as pemphigus, bullous dermatitis herpetiformis, severe erythema multiforme (Stevens-Johnson syndrome), exfoliative dermatitis, mycosis fungoides, psoriasis, and seborrheic dermatitis;

e) allergic states, such as seasonal or perennial allergies, allergic rhinitis, bronchial asthma, contact dermatitis, atopic dermatitis, serum sickness, and drug hypersensitivity reactions;

f) ophthalmic diseases and conditions, such as allergic corneal marginal ulcers, herpes zoster ophthalmicus, anterior segment inflammation, diffuse posterior uveitis and choroiditis, chronic uveitis, sympathetic ophthalmia, allergic conjunctivitis, keratitis, chorioretinitis, optic neuritis, iritis and iridocyclitis;

g) respiratory diseases, such as symptomatic sarcoidosis, Loeffler's syndrome, berylliosis, fulminating or disseminated pulmonary tuberculosis, and aspiration pneumonitis;

h) hematologic disorders, such as idiopathic thrombocytopenic purpura, secondary thrombocytopenia, acquired (autoimmune) hemolytic anemia, erythroblastopenia (RBC anemia), and congenital (erythroid) hypoplastic anemia;

i) neoplastic diseases, such as leukemia and lymphoma;

j) edematous states, such as inducing diuresis or emission of proteinuria in the nephrotic syndrome, without uremia, of the idiopathic type or that due to lupus erythematosus;

k) gastrointestinal diseases, such as ulcerative colitis, regional enteritis, inflammatory bowel disease, Crohn's disease, gastritis, irritable bowel syndrome;

l) miscellaneous conditions, such as tuberculous meningitis and trichinosis; and m) neurological conditions, such as Alzheimer's disease, Parkinson's disease, Huntington's disease, amyotrophic lateral sclerosis, spinal cord injury, psychotic major depression, and peripheral neuropathy.

A condition mediated by glucocorticoid receptor activity also includes transplant rejection (e.g., kidney, liver, heart, lung, pancreas (e.g., islet cells), bone marrow, cornea, small bowel, skin allografts, skin homografts (such as employed in burn treatment), heart valve xenografts, serum sickness, and graft vs. host disease, autoimmune diseases, such as rheumatoid arthritis, psoriatic arthritis, multiple sclerosis, Type I and Type II diabetes, juvenile diabetes, obesity, asthma, inflammatory bowel disease (such as Crohn's disease and ulcerative colitis), pyoderma gangrenum, lupus (systemic lupus erythematosis), myasthenia gravis, psoriasis, dermatitis, dermatomyositis; eczema, seborrhoea, pulmonary inflammation, eye uveitis, hepatitis, Grave's disease, Hashimoto's thyroiditis, autoimmune thyroiditis, Behcet's or Sjorgen's syndrome (dry eyes/mouth), pernicious or immunohaemolytic anaemia, atherosclerosis, Addison's disease (autoimmune disease of the adrenal glands), idiopathic adrenal insufficiency, autoimmune polyglandular disease (also known as autoimmune polyglandular syndrome), glomerulonephritis, scleroderma, morphea, lichen planus, viteligo (depigmentation of the skin), alopecia areata, autoimmune alopecia, autoimmune hypopituitarism, Guillain-Barre syndrome, and alveolitis; T-cell mediated hypersensitivity diseases, including contact hypersensitivity, delayed-type hypersensitivity, contact dermatitis (including that due to poison ivy), uticaria, skin allergies, respiratory allergies (hayfever, allergic rhinitis) and gluten-sensitive enteropathy (Celiac disease); inflammatory diseases such as osteoarthritis, acute pancreatitis, chronic pancreatitis, acute respiratory distress syndrome, Sezary's syndrome and vascular diseases which have an inflammatory and or a proliferatory component such as restenosis, stenosis and artherosclerosis.

A condition mediated by glucocorticoid receptor activity also includes:

a) asthma of whatever type, etiology, or pathogenesis, in particular asthma that is a member selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis;

b) chronic or acute bronchoconstriction, chronic bronchitis, small airways obstruction, and emphysema;

c) obstructive or inflammatory airways diseases of whatever type, etiology, or pathogenesis, in particular an obstructive or inflammatory airways disease that is a member selected from the group consisting of chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension;

d) bronchitis of whatever type, etiology, or pathogenesis, in particular bronchitis that is a member selected from the group consisting of acute bronchitis, acute laryngotracheal bronchitis, arachidic bronchitis, catarrhal bronchitis, croupus bronchitis, dry bronchitis, infectious asthmatic bronchitis, productive bronchitis, *staphylococcus* or streptococcal bronchitis and vesicular bronchitis, acute lung injury; and e) bronchiectasis of whatever type, etiology, or pathogenesis, in particular bronchiectasis that is a member selected from the group consisting of cylindric bronchiectasis, sacculated bronchiectasis, fusiform bronchiectasis, capillary bronchiectasis, cystic bronchiectasis, dry bronchiectasis and follicular bronchiectasis.

Another embodiment includes a use of a compound or salt of the present invention for use in treating obstructive or inflammatory airways diseases of whatever type, etiology, or pathogenesis, in particular an obstructive or inflammatory airways disease that is a member selected from the group consisting of chronic eosinophilic pneumonia, chronic obstructive pulmonary disease (COPD), COPD that includes chronic bronchitis, pulmonary emphysema or dyspnea associated or not associated with COPD, COPS that is characterized by irreversible, progressive airways obstruction, adult respiratory distress syndrome (ARDS), exacerbation of airways hyper-reactivity consequent to other drug therapy and airways disease that is associated with pulmonary hypertension, or asthma of whatever type, etiology, or pathogenesis, in particular asthma that is a member selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cord air induced asthma, occupational asthma, infective asthma caused by bacterial, fungal, protozoal, or viral infection, non-allergic asthma, incipient asthma, wheezy infant syndrome and bronchiolytis.

The present invention includes a method of treating an inflammation related condition in a subject comprising administering to the subject a compound or salt of the present invention.

The present invention includes a method of treating conditions such as asthma, dermatitis, inflammatory bowel disease, Alzheimer's disease, psychotic major depression, neuropathy, transplant rejection, multiple sclerosis, chronic uveitis, or chronic obstructive pulmonary disease in a subject comprising administering to the subject a compound or salt of the present invention.

The present invention includes a method of treating rheumatoid arthritis in a subject comprising administering to the subject a compound or salt of the present invention.

Rheumatoid arthritis is considered a chronic autoimmune and inflammatory disease producing inflamed joints, which eventually swell, become painful, and experience degradation of cartilage, bone, and ligaments of the joint. A result of rheumatoid arthritis is deformity, instability, and stiffness of the joint and scarring within the joint. The joints deteriorate at a highly variable rate. Many factors, including genetic predisposition, may influence the pattern of the disease. People with rheumatoid arthritis may have a mild course, occasional flare-ups with long periods of remission without disease, or a steadily progressive disease, which may be slow or rapid. Rheumatoid arthritis may start suddenly, with many joints becoming inflamed at the same time. More often, it starts subtly, gradually affecting different joints. Usually, the inflammation is symmetric, with joints on both sides of the body affected. Typically, the small joints in the fingers, toes, hands, feet, wrists, elbows, and ankles become inflamed first, followed by the knees and hips.

Pain associated with rheumatoid arthritis is typically somatic nociceptive joint pain. Swollen wrists can pinch a nerve and result in numbness or tingling due to carpal tunnel syndrome. Cysts may develop behind affected knees, can rupture, causing pain and swelling in the lower legs.

The present invention includes a method of treating dermatitis in a subject comprising administering to the subject a compound or salt of the present invention.

The present invention includes a method of treating chronic obstructive pulmonary disease in a subject comprising administering to the subject a compound or salt of the present invention.

The present invention includes a method of treating asthma in a subject comprising administering to the subject a compound or salt of the present invention.

The present invention includes a method of treating Alzheimer's disease in a subject comprising administering to the subject a compound or salt of the present invention.

The present invention includes a method of mitigating side effects associated with glucocorticoid receptor modulation, comprising administering a compound of Formula I to a subject.

The present invention includes a method of mitigating side effects associated with prednisolone treatment, comprising administering a compound of Formula I to a subject.

The present invention further comprises methods of treating the aforementioned conditions, diseases, and disorders in a subject or a subject susceptible to having such a condition, by administering to the subject one or more compounds or salts of the present invention.

In one embodiment, the aforementioned treatment is preventative treatment.

In another embodiment, the aforementioned treatment is palliative treatment.

In another embodiment, the aforementioned treatment is restorative treatment.

E. DOSAGE AND ADMINISTRATION

To select the most appropriate dosage form and route of administration for treatment of the proposed indication, the compounds or salts of the invention can be assessed for their biopharmaceutical properties, such as solubility and solution stability (across pH), and permeability.

Doses for compounds or salts of the invention range from 0.1 mg to 100 mg for oral administration and doses range from 2 mg or less for inhaled administration. The dose may be administered in single or divided doses and may fall outside of the typical range given herein.

The dosages are based on an average human subject having a weight of about 60 kg to 70 kg. Dosing and dosing regimen depend upon subject and a variety of conditions that may affect dosing (age, sex, body weight, etc.). The physician will readily be able to determine doses for subjects whose weight falls outside this range, such as infants and the elderly.

Oral Administration

The compounds of the invention and salts thereof may be administered orally. Oral administration may involve swallowing, so that the compound or salt enters the gastrointestinal tract, and/or buccal, lingual, or sublingual administration by which the compound or salt enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches. Further, the compound or salts of the invention can be administered as a spray dried dispersion.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention and salts thereof may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Pharmaceutical Technology On-line, 25(2), 1-14, by Verma et al (2001).

Dose ranges for oral administration also include from 0.1 mg to −80 mg, 15 mg to 80 mg, 0.1 mg to 25 mg.

Parenteral Administration

The compounds or salts of the invention may also be administered directly into the blood stream, into muscle, or into an internal organ. Example 2 could be administered into the blood stream. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of the present invention and salts thereof used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(dl-lactic-coglycolic)acid (PGLA) microspheres.

Topical Administration

The compounds or salts of the invention may also be administered topically, (intra)dermally, or transdermally to the skin or mucosa. Example 1 could be administered to the skin. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

Inhaled/Intranasal Administration

The compounds or salts of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurized container, pump, spray, atomizer, or nebuliser contains a solution or suspension of the compounds) of the invention comprising, for example, ethanol, aqueous ethanol, or a suitable alternative agent for dispersing, solubilising, or extending release of the active, a propellants) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insulator may be formulated to contain a powder mix of the compound of the invention, a suitable powder base such as lactose or starch and a performance modifier such as L-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics may comprise a compound of the present invention, propylene glycol, sterile water, ethanol and sodium chloride. Alternative solvents which may be used instead of propylene glycol include glycerol and polyethylene glycol.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" which may be administered in a single dose or, more usually, as divided doses throughout the day.

Dose ranges for inhaled administration range from 2 mg to less or 1 mg to less.

Combination

The compounds or salts of the invention may be administered in combination with one or more other therapeutic agents, such as a drug. The compound of the present invention or salt thereof may be administered at the same time or different time as one or more other therapeutic agents.

For example, "in combination" includes: simultaneous administration of a combination of compound or salt of the invention and a therapeutic agent to a subject, when such components are formulated together into a single dosage form which releases said components at substantially the same time to said subject; substantially simultaneous administration of a combination of compound or salt of the invention and a therapeutic agent to a subject in need of treatment, when such components are formulated apart from each other into separate dosage forms which are taken at substantially the same time by said subject, whereupon said components are released at substantially the same time to said subject; sequential administration of a combination of compound or salt of the invention and a therapeutic agent to a subject, when such components are formulated apart from each other into separate dosage forms which are taken at consecutive times by said subject with a significant time interval between each administration, whereupon said components are released at substantially different times to said subject; and sequential administration of such combination of compound or salt of the invention and a therapeutic agent to a subject, when such components are formulated together into a single dosage form which releases said components in a controlled manner whereupon they are concurrently, consecutively, and/or overlappingly administered at the same and/or different times by said subject, where each part may be administered by either the same or different route.

For example, the compounds or salts of the present invention may be used in combination, partially or completely, in addition to other antiinflammatories. Suitable antiinflammatories include cyclosporine, zoledronic acid, efalizumab, alefacept, etodolac, lornoxicam, OM-89, valdecoxib, tocilizumab, abatacept, meloxicam, etanercept, nambumetone, rimexolone, 153Sm-EDTMP, prosorba, imidazole salicylate, oprelvekin, hylauronic acid, naproxen, piroxicam, diacerein, lumericoxib, tacrolimus, aceclofenac, actarit, tenoxicam, rosiglitazone, deflazacort, adalimumab, leflunomide, risedronate sodium, misoprostol and diclofenac, SK-1306X, infliximab, anakinra, celecoxib, diclofenac, etoricoxib and felbinac, reumacon, golimumab, denosumab, ofatumumab, 10rT1 antibody, pelubiprofen, licofelone, temsirolimus, eculizumab, iguratimod, and prednisone. Other suitable antiinflammatories include CP-481715, ABN-912, MLN-3897, HuMax-IL-15, RA-1, paclitaxel, Org-37663, Org 39141, AED-9056, AMG-108, fontolizumab, pegsunercept, pralnacasan, apilimod, GW-274150, AT-001, 681323 (ASK) K-832, R-1503, ocrelizumab, DE-096, Cpn10, THC+CBD (GW Pharma), 856553 (GSK), ReN-1869, immunoglobulin, mm-093, amelubant, SCIO-469, ABT-874, LenkoVAX, LY-2127399, TRU-015, KC-706, dipyridamole, amoxapinet and dipyridamole, TAK-715, PG 760564, VX-702, prednisolone and dipyridamole, PMX-53, belimumab, prinaberel, CF-101, tgAAV-TNFR:Fc, R-788, prednisolone and SSRI, dexamethasone, CP-690550 and PMI-001.

One of ordinary skill in the art will also appreciate that when using the compounds of the invention or salts thereof in the treatment of a specific disease that the compounds of the invention may be combined with various existing therapeutic agents used for that disease.

For example, the compounds or salts of the invention may be combined with agents that modulate one or more of the following targets: Cyclooxygenase 2 (prostaglandin endoperoxide synthase 2); TNF-R (tumor necrosis factor receptor type 1); Cyclooxygenase (Cox 1 and 2; Non-specific); Map Kinase p38 (Non-specific); Il1 receptor (type I and II, Non-specific); Arachidonate 5-lipoxygenase; Glucocorticoid receptor (GR); NF-kB; Tumour necrosis factor (TNF-alpha); CCR1 chemokine receptor; Leukotriene B4 receptor (Non-specific); PDE4 (Phosphodiesterase 4; Non-specific); IL6 receptor; Integrin (Non-specific); ADAM-17 (TNF-alpha converting enzyme); ICE (Caspase 1/interleukin-1 beta convertase); Prostaglandin Synthesis enzymes (Non-specific); Substance-P receptor (SPR/NK-1 receptor); Prostanoid receptor (Non-specific); Vascular cell adhesion protein 1 (VCAM 1); MMP-13 (collagenase 3); VEGF Receptor (Non-specific); C5A anaphylatoxin chemotactic receptor (C5AR); Macrophage migration inhibitory factor (MIF); Purine nucleoside phosphorylase (PNP); Beta 1 interferon; MMP-3 (stromelysin 1); CCR2 chemokine receptor; MMP-2 (gelatinase A); Tumor necrosis factor receptor 5 (CD40); CD44 antigen (homing function and Indian blood group system); CCR5 chemokine receptor; Prostaglandin E synthase; Peroxisome proliferator activated receptor gamma (PPAR-gamma); CXCR4 chemokine receptor; Cathepsin S; Proto-oncogene LCK tyrosine kinase; CXCR3 chemokine receptor; PDGF Receptor; FKBP (12 FK-506); Ig superfamily CTLA-4; Protein Kinase C (PKC, Non-specific); Integrin alpha-V/beta-5; Cathepsin K; 26S Proteasome; Mineralocorticoid receptor (MR); IkB kinase beta subunit (IKK BETA); Platelet activating factor receptor (PAF-R); Farnesyl pyrophosphate FPP synthetase; CXCR1 chemokine receptor; Macrophage colony stimulating factor I receptor (CSF-1R); IL18 receptor 1; Adenosine A3 receptor; Granulocyte-macrophage colony-stimulating factor (GMCSF); SYK tyrosine kinase; CRF receptor (Non-specific); Alpha/Beta tubulin heterodimer; Tyrosine kinase (Non-specific); Amyloid beta; Macrophage colony stimulating factor (MCSF); Tumor necrosis factor ligand superfamily member 11 (receptor activator of nuclear factor kappa b ligand); Phospholipase (Non-specific); Estrogen receptor (alpha/beta; Non-specific); MMP-9 (gelatinase B); Nitric oxide synthase (Non-specific); Inducible Nitric Oxide Synthase (Non-specific); p53 cellular tumor antigen; Insulin-like growth factor 1 (somatomedin C); Nicotinic acetylcholine receptor complex; Mu-type opioid receptor (MOR-1); IL 11; ERBB/EGF Receptor Tyrosine Kinase (Non-specific); Histamine H2 receptor; Dipeptidyl peptidase IV (DPP IV, CD6); Topoisomerase II; CCR7 chemokine receptor; Bacterial Dihydrofolate Reductase (Non-specific); Beta-tubulin; DNA polymerase (Human, any subunit composition); CCR4 chemokine receptor; CCR3 chemokine receptor; K+ (potassium) Channel (Non-specific); Mitogen-activated protein kinase 14 (MAPK14/P38-alpha); L-type calcium channels (Non-specific); CCR6 chemokine receptor; PDE3 ((Phosphodiesterase 3; Non-specific); Cysteine protease (Non-specific); Sodium-dependent noradrenaline transporter (NAT); MAP2Kinase (MEKs; Non-specific); RAF Kinase (Non-specific); Hypoxia-inducible factor 1 alpha; NMDA receptor; Estrogen receptor beta (ER-beta); Human DNA; Cholecystokinin type B receptor (CCKB); B1 bradykinin receptor (BK1); P2X purinoceptor 7 (P2x7); Adenosine A2A receptor; Cannabinoid receptor 2 (CB2); Sigma opioid receptor; Cannabinoid receptor 1 (CB1); CXCR2 chemokine receptor; Complement factor I (C3B/C4B inactivator); Protein Kinase B (RAC-Kinase) (Non-specific); Gamma secretase complex; CRTH2 (GPR44); p53-associated gene (MDM2 ubiquitin-protein ligase E3); VIP receptor (Non-specific); IL1 receptor, type I; IL6 (interferon, beta 2); MMP (Non-specific); Insulin; MMP-2/3/9; Calcitonin/calcitonin-related polypeptide, alpha; Lipoxygenase (Non-specific); vascular endothelial growth factor (VEGF); Thrombin; Androgen receptor; Map Kinase (Non-specific); Sex hormone-binding globulin; Chemokine CCL2 (MCP1/MCAF); Phospholipase A2; Erythropoietin (EPO); Plasminogen; Gastric proton pump (H+ K+ ATPase); Caspase (Non-specific); FGF receptor (Non-specific); Peroxisome proliferator activated receptor alpha (PPAR-alpha); MIP1a receptor (Non-specific); S100 calcium-binding protein (Non-specific); PGE receptor (Non-specific); peptidyl arginine deiminase, type IV; PDGF (a/b) complex; Beta-Lactamase and PBPs (Cell wall biosynthesis); Opioid receptor (Non-specific); Angiotensin-converting enzyme 1 (ACE1); Urokinase-type plasminogen activator (UPA); Phosphodiesterase (Non-specific PDE); Progesterone receptor (PR); 5HT (serotonin) receptor (Non-specific); tumor necrosis factor (ligand) superfamily, member 5 (CD40 ligand); Thymidylate synthase; Integrin Alpha4-Paxillin interaction; Integrin alpha-4 (VLA-4/CD49D); ERK1; glucose phosphate isomerase (autocrine motility factor); Dopamine receptor (Non-specific); Chemokine CXCL12 (SDF-1); Microsomal triglyceride transfer-protein; Integrin alpha-5/beta-1; Signal transducer and activator of transcription 3 (acute-phase response factor); Plasminogen activator inhibitor-1 (PAI-1); Vitamin D3 receptor (VDR/1,25-dihydroxyvitamin D3 receptor); Aromatase complex (P450 arom and NADPH-cytochrome P450 reductase); Protein tyrosine phosphatase (Non-specific); 3-hydroxy-3-methylglutaryl coenzyme A (HMG-CoA) reductase; Integrin beta-1 (Fibronectin receptor beta subunit); Integrin beta-1/alpha-11; P Selectin (GMP140/granule membrane protein-140); Five-lipoxygenase activating protein (SLAP); H+/K+ ATPase (Non-specific); Na+ (sodium) Channel (Non-specific); Thyroid peroxidase; Brain voltage gated sodium channel alpha-1; Beta-2 adrenergic receptor; BCL1 (Cyclin D1); Thyroid hormone receptor (Non-specific); Vascular endothelial growth factor receptor 2 (VEGFR-2/FLK1); Alpha-V/Beta-6 Integrin; integrin alpha-V (Vitronectin receptor alpha subunit/CD51); SRC Kinase; Pleiotrophin (heparin binding growth factor 8, neurite growth-promoting factor 1); osteopontin (secreted phosphoprotein 1); toll-like receptor 4 (TLR4); Vanilloid receptor (Non-specific); Pi3Kinase (Non-specific); Poly(ADP-ribose) polymerase (PARP); PPAR receptor (Non-specific); Beta adrenergic receptor (Non-specific); transient receptor potential cation channel, subfamily V, member 1 (TRPV1); Topoisomerase I; Histamine H1 receptor; kininogen; IKK Kinase (Non-specific); HIV TAT protein; Toll-like receptor 2; solute carrier family 22 (organic cation transporter), member 4 (SLC22A4); RXR receptor (Non-specific); Renin (Angiotensinogenase); Gonadotropin-releasing hormone receptor (GNRH-R); Penicillin Binding Proteins (Cell wall peptidases); Calmodulin; Mitogen-activated protein kinase 1 (MAPK1/ERK2); Calcium channel (Non-specific); Aggrecanase (non-specific); JNK kinase (Non-specific); transthyretin (TTR); CX3CR1 receptor; Coagulation factor III (thromboplastin, tissue factor); Sodium-dependent serotonin transporter (5HTT); Colony stimulating factor 1 (macrophage); Tissue Transglutaminase (Transglutaminase 2/TGM2); Advanced glycosylation end product-specific receptor; Monoamine oxidase (A and B; Non-specific); Histamine receptor (Non-specific); Sodium-dependent dopamine transporter (DAT); Thrombopoietin (myeloproliferative leukemia virus oncogene ligand, megakaryocyte growth and development factor); Signaling lymphocytic activation molecule; Neutral endopeptidase (NEP/Neprilysin); Endothelin-1 receptor (ETA); Tyrosinase; Mitogen-activated protein kinase 8 (MAPK8/JNK1); IAP (inhibitor of apoptosis) non-specific; Phosphoinositide 3-kinase; Prostaglandin F2-alpha receptor (Prostanoid FP receptor); Human growth hormone; Vasopressin receptor (Non-specific); Mast/stem cell growth factor receptor (C-KIT); CDK (Non-specific); D415HT1a (Dopamine D4 receptor, serotonin receptor 1a); Angiopoietin 1 receptor (TIE-2) (TEK); Estrogen receptor alpha (ER-alpha); Epidermal growth factor receptor; Focal Adhesion Kinase (Non-specific); Peripheral benzodiazepine receptor (HPBS); Oxytocinase; Cytosolic phospholipase A2; Endopeptidase (Non-specific); FGFR1 FGF receptor 1; Neurokinin NK1/NK2 receptor; Prolyl 4-hydroxylase complex; Integrin alpha-5 (Fibronectin receptor alpha subunit/VLA-5/CD49E); Muscarinic acetylcholine receptor (Non-specific); Tyrosine-protein kinase JAK3 (JANUS KINASE 3); odc1—ornithine decarboxylase; 5HT3 receptor; Adrenomedullin; Phosphatidylinositol 3-kinase homolog (ataxia-telangiectasia mutated gene/ATM); Erythropoietin receptor; Connective tissue growth factor; RAC-alpha serine/threonine kinase (Protein kinase B); Toll-like receptor 9; Neuronal nitric oxide synthase (NOS1); Kappa-type opioid receptor (KOR-1); Cardiac Na+ channel complex; ERBB-2 receptor protein tyrosine kinase (Tyrosine kinase-type cell surface receptor HER2); Thrombin receptor (PAR-1); PDE4B (cAMP-specific phosphodiesterase 4B/HSPDE4B); Platelet-derived growth factor beta polypeptide; FKBP-rapamycin associated protein (FRAP, mTOR); thrombomodulin; HIV Protease (retropepsin); PDE4D (cAMP-specific phosphodiesterase 4D/HSPDE4D); Adenosine kinase; Histone Deacetylase (Non-specific); Prostaglandin E2 receptor EP4 subtype (Prostanoid EP4 receptor); Mitogen-activated protein kinase kinase 3 (MAP2K3); MMP-12 (metalloelastase); OX40 receptor; Non specific human ubiquitin ligase; Sulfonylurea receptor (SUR1 (pancreatic) and SUR2 (cardiac/smooth muscle)); Coagulation factor X (Stuart factor); MAP kinase activated protein kinase 2 (MAPKAPK-2); IgE heavy chain constant region; Dopamine D2+5HT2A receptors; 5-hydroxytryptamine 4 receptor (5HT4); Type-1 angiotensin II receptor (AT1); Cytochrome P450 3A4; T-cell cyclophilin (cyclophilin A); Neuromedin K receptor (NKR/NK-3 receptor); Leukotriene B4 receptor; Brutons tyrosine kinase (BTK); Mitogen-activated protein kinase kinase 6 (MAP2K6); endoglin; M1/D2/5HT2; Sodium Dependent Noradrenaline transporter+Dopamine D4 receptor; Mitogen-activated protein kinase kinase 4 (MAP2K4); Heat shock protein Hsp90 A/B; Histidine decarboxylase; solute carrier family 22 (organic cation transporter), member 5 (SLC22A5); CSK tyrosine kinase; Prolyl endopeptidase; Cysteinyl leukotriene receptor (CYSLT1); Nuclear receptor NURR1 (Immediate-early response protein NOT); Toll-like receptor 3; Proteinase activated receptor 2 (PAR-2); Prostacyclin receptor (prostanoid IP receptor); Serine (or cysteine) proteinase inhibitor, clade F (alpha-2 antiplasmin, pigment epithelium derived factor), member 1; Pituitary adenylate cyclase activating polypeptide type i receptor (PACAP-R-1); Tumor necrosis factor (ligand) superfamily, member 10; C-MAF (short form); Acetylcholinesterase (ACHE); Alpha1 adrenergic receptor (Non-specific); GABA A Receptor Bz binding; Lysosphingolipid receptor EDG-1; Mucosal addressing cell adhesion molecule-1 (MAdCam); alpha-1L adrenergic receptor; Hepatocyte growth factor receptor (MET Proto-oncogene tyrosine kinase); Muscarinic acetylcholine receptor M3; MEK1; Insulin receptor; GABA receptor (A+B; Nonspecific); Phosphatidylinositol 3-kinase catalytic subunit gamma (PI3 kinase gamma); Bone morphogenetic protein 2 (BMP2); SKY tyrosine protein kinase receptor (TYRO3) (RSE); discoid in domain receptor family, member 2 (DDR2); KV Voltage-gated potassium channel (Non-specific); Sphingosine kinase (Non-specific); High affinity nerve growth factor receptor (TRK-A); Carbonic Anhydrases (all); Thrombopoietin receptor; Vascular endothelial growth factor C; angiotensinogen; ATP-binding cassette, sub-family B (MDR/TAP), member 1 (ABCB1) (Multidrug resistance P-glycoprotein (MDR1); Mitogen-activated protein kinase kinase 7 (MAP2K7); Muscarinic acetylcholine receptor M1; HIV Reverse transcriptase; PDE5A (cGMP-binding, cGMP-specific phosphodiesterase 5A/HSPDE5A); Alpha adrenergic receptor (Non-specific); Lipoprotein-associated coagulation inhibitor; Carboxypeptidase B2 (TAFI); Cholinesterase (Non-specific); B2 bradykinin receptor (BK2); Aldose reductase; Coagulation factor XI (Plasma thromboplastin antecedent); Serine/threonine protein kinase P78; Methionine aminopeptidase 2; Soluble guanylate cyclase (Non-specific); Ribosomal protein S6 kinase; Metabotropic glutamate receptor 1; Non-receptor tyrosine-protein kinase TYK2; Metabotropic glutamate receptor (Non-specific); Vascular endothelial growth factor receptor 3 (VEGFR-3/FLT4); Mitogen-activated protein kinase 13 (MAPK13/P38 delta); Fibroblast activation protein (seprase); Corticotropin releasing factor receptor 1 (CRF1); Mitogen-activated protein kinase 11 (MAPK11/P38 beta); Complement component 5; FL cytokine receptor (FLT3); AMPA receptor (Glutamate receptors 1-4); Nerve growth factor receptor; Acyl-CoA A: cholesterol acyltransferase 1 (ACAT1); Frizzled-like receptor smoothened homolog (SMO); G-protein-coupled receptor BONZO (STRL33, CXCR6); IKCa proteins; TGF-beta receptor type II (TGFR-2); HIV-vif protein; 5-hydroxytryptamine 2B receptor (5HT2B); Fatty acid binding protein (Non-specific); Toll-like receptor 7 (TLR7); Ghrelin; CD36 antigen (collagen type I receptor, thrombospondin receptor); Mitogen-activated protein kinase kinase kinase 3 (MAP3K3/MEKK3); FMLP-related receptor I (FMLP-RI); Sphingosine kinase SPHK1; Histidyl-tRNA synthetase; Mitogen-activated protein kinase 9 (MAPK9/JNK2); P2X receptor (Non-specific); Casein kinase I (Non-specific); Sulfotransferases (non specific); Nuclear receptor ROR-alpha-1; Catechol O-methyltransferase (COMT); Monoamine oxidase A (MAOA); Gamma-glutamyl hydrolase; Protein kinase C alpha type (PKC-alpha); Mitogen-activated protein kinase 12 (MAPK12/ERK6/P38 gamma); Alpha2Delta Calcium Channel; Tissue Factor/Factor VIIa complex; Hookworm neutrophil inhibitory factor; IKr potassium channel; Histamine H4 receptor (JAR3) (PFI-13); 5-hydroxytryptamine 2A receptor (5HT2A); Cholecystokinin type A receptor (CCKA); 11-beta hydroxysteroid dehydrogenase 1; Growth hormone releasing hormone; Nicotinic acetylcholine receptor protein alpha-7; 5HT2 receptor (Non-specific); Sodium/hydrogen exchanger isoform 1 (NHE1); Substance-K receptor (SKR/NK-2 receptor); 5-hydroxytryptamine 1D receptor (5HT1D); 5HT1B/1D Receptors; Sucrase-isomaltase; Beta-3 adrenergic receptor; Calcitonin gene-related peptide (GGRP) type 1 receptor; Cyclin-dependent kinase 4 (CDK4); Alpha-1A adrenergic receptor; P2Y12 platelet ADP receptor; Mitogen-activated protein kinase kinase kinase 5 (MAP3K5) (MEKK5); regulator of G-protein signalling 2; Interleukin-1 receptor-associated kinase (IRAK); Inorganic pyrophosphatase (ppase); ITK/TSK tyrosine kinase; RAR gamma; AXL tyrosine protein kinase (UFO, GAS6 receptor); Activin receptor-like kinase 1 (ALK-1); Runt-related transcription factor 2; AMP deaminase (Non-specific); CCR8 chemokine receptor; CCR11 chemokine receptor; Nociceptin receptor; Insulin-like growth factor I receptor; P2Y Receptor (Non-specific); Protein kinase C theta type (NPKC-theta); DNA-methyltransferase non-specific; Phosphorylase Kinase (Non-specific); C3A anaphylatoxin chemotactic receptor (C3AR); sphingosine kinase 2 (SPHK2); Casein kinase II non-specific; Phosphoglycerate kinase 1; UDP-Gal:beatGlcNAc beta 1,4-galactosyltransferase 2 (B4GALT2); sapiens solute carrier family 7 (cationic amino acid transporter, y+ system), member 5 (SLC7A5); MMP-17 (MT-MMP 4); Casein kinase II alpha chain (CK II); Growth arrest specific 6 (GAS6); MAP kinase activated protein kinase 3 (MAPKAPK-3); Mitogen and stress-activated protein kinase-1 (MSK1); Prostaglandin D2 synthase (21 kD, brain); Pancreatic K+ channel (Non-specific); TGF-beta receptor type I (TGFR-1/Activin receptor-like kinase 5/ALK-5); Cyclin-dependent kinase 2 (CDK2); ACAT (ACAT Enzymes 1 and 2; Non-specific); Delta-type opioid receptor (DOR-1); 5-hydroxytryptamine 6 receptor (5HT6); 5-hydroxytryptamine 1A receptor (5HT1A); 5HT1 receptor (Non-specific); Growth hormone receptor; PDE7 (Phosphodiesterase 7; Non-specific); IgE receptor (R1 and R2; Non-specific); Cyclin-dependent kinase 1 (CDK1); Farnesyl-protein transferase complex; Prostaglandin D2 receptor (prostanoid DP receptor); Complement C1S component; Histone deacetylase 5; dickkopf homolog 1 precursor; P2X purinoceptor 4 (P2×4); Lectin-like oxidized LDL receptor (LOX-1); Epoxide hydrolase 2 (trans-styrene oxide hydrolase) (soluble epoxide hydrolase) (sEH); dihydrodipicolinate synthase (dhdps) (DapA); CaM Kinase II Complex; LXR alpha/beta (Non-specific LXR); Second mitochondria-derived activator of caspase; Integrin-linked kinase (ILK); Focal adhesion kinase 2 (FADK 2); Adenosine A2B receptor; WEE1-like protein kinase; Checkpoint kinase (CHK2); Bacterial SecA protein; Nicotinic acetylcholine receptor protein beta-2; Mitogen-activated protein kinase kinase 1 (MAP3K1/MEKK1); Protein kinase C zeta type (NPKC-zeta); PDK1 (3-phosphoinositide-dependent protein kinase-1); 5-hydroxytryptamine 5A receptor (5HT5A); Steroid 5-alpha-reductase; Mitogen-activated protein kinase kinase kinase 8 (MAP3K8/COT); Protein tyrosine phosphatase 1B; P2Y purinoceptor 1 (P2Y1); Alpha-1D adrenergic receptor; Casein kinase I epsilon (CKI-epsilon); 5-hydroxytryptamine 7 receptor (5HT7); Coagulation factor VII (Eptacog alfa); Pyruvate dehydrogenase kinase (PDHK; Non-specific); PDE7A (cAMP-specific phosphodiesterase 7A/HSPDE7A); Glucagon-like peptide 1 receptor (GLP-1R); Influenza rna polymerase subunit p3 (pb2 endonuclease); Viral protease (Non-specific); Topoisomerase IV; Parathyroid hormone receptor (PTH2 receptor); Protein kinase C beta-I type (PKC-beta-1); Dopamine beta hydroxylase; Galactosyltransferase associated protein kinase P58/GTA; Presynaptic protein SAP97; synovial apoptosis inhibitor 1, synoviolin (SYVN1) (HRD1) (HRD-1); Squalene epoxidase (ERG1); Protein kinase C epsilon type (NPKC-epsilon); Corticotropin releasing factor receptor 2 (CRF2); Intermediate conductance calcium-activated potassium channel (IK1); Nucleoside diphosphate kinase A (NDKA) (NM23-H1); Interleukin-1 receptor associated kinase 4 (IRAK-4); Glycogen synthase kinase-3 alpha (GSK-3 alpha); solute carrier family 22 (organic cation transporter), member 2 (SLC22A2); Pyruvate dehydrogenase kinase 1 (PDK1); PAK-alpha kinase (PAK-1); Human 14-3-3 proteins; isoleucyl-tRNA synthetase; Prenylcysteine carboxyl methyltransferase (PCCMT); CKLF1; and NAALADase II.

The compounds or salts of the invention may further be administered in combination with one or more agents such as SSRI, matrix metalloproteinase (MMP) inhibitors, aggrecanase inhibitors, inducible nitric oxide (iNOS) inhibitors, inhibitors of insulin-like growth factor (IGF) expression or activity, inhibitors of fibroblast growth factor (FGF) expression or activity, inhibitors of CD 44 expression or activity, inhibitors of interleukin (IL) expression or activity, inhibitors of tumor necrosis factor alpha (TNF-alpha) expression or activity, inhibitors of tumor necrosis factor-inducible protein 6 (TSG-6) expression or activity, inhibition of Bikunin expression or activity, inhibitors of beta-secretase (BACE), inhibitors of PACE-4, inhibition of nuclear receptor rev-ErbA alpha (NR1D1) expression or activity, inhibition of endothelial differentiation sphingolipid G-protein-coupled receptor 1 (EDG-1) expression or activity, inhibition of proteinase-activated receptor (PAR) expression or activity, inhibition of cartilage-derived retinoic-acid-sensitive protein (CD-RAP) expression or activity, inhibitors of protein kinase C zeta (PKCz), inhibition of resistin expression or activity, inhibition of a disintegrin and metalloproteinase 8 (ADAM8), inhibition of complement component 1 s subcomponent (C1s) expression or activity, inhibition of formyl peptide receptor-like 1 (FPRL1) expression or activity.

Additional examples of agents useful in combination with compounds or salts of the invention include inhibitors of MMP-2, -3, -9, or -13; inhibitors of aggrecanase-1 or -2; inhibitors of IGF-1 or -2 expression or activity; inhibitors of FGF-2, -18, or -9 expression or activity; and inhibitors of IL-1, -4 or -6 expression or activity.

Further examples of agents useful in combination with compounds or salts of the invention include IGF-1 or -2 antibodies; FGF receptor-2 or -3 antagonists, CD 44 antibodies, IL-1, -4 or -6 antibodies, TNF-alpha antibodies; TSG-6 antibodies; bikunin antibodies; NR1D1 antagonists; EDG-1 antagonists; PAR antagonists, CD-RAP antibodies, resistin antibodies, C1s antibodies, and FPRL1 antibodies.

Additional examples of compounds that can be administered with the compounds or salts of the present invention include: Cyclooxygenase-2 (COX-2) selective inhibitors such as celecoxib, rofecoxib, parecoxib, valdecoxib, deracoxib, etoricoxib, and lumiracoxib; opioid analgesics such as morphine, hydromorphone, oxymorphone, fentanyl, codeine, dihydrocodeine, oxycodone, hydrocodone, buprenorphine, tramadol, and nalbuphine; nonsteroidal antiinflammatory drugs (NSAIDs) such as aspirin, diclofenac, diflunisal, ibuprofen, fenoprofen, naproxen, nepafenac, and acetaminophen; Phosphodiesterase V inhibitors (PDEV) such as sildenafil; alpha-2-delta ligands such as gabapentin and pregabalin; and local anaesthetics such as benzocaine, lidocaine, ropivacaine, menthol, camphor and methyl salicylate.

Examples of other types of compounds and classes of compounds that can be used in combination with the compounds or salts of the present invention include: analgesics, barbiturate sedatives; benzodiazepines; Histamine $H_1$ antagonists having a sedative action; sedatives; skeletal muscle relaxants; N-methyl-D-aspartic acid (NMDA) receptor antagonists; alpha-adrenergics; tricyclic antidepressants; anticonvulsants such as carbamazepine; tachykinin (NK) antagonists, particularly NK-3, NK-2 or NK-1 antagonists; muscarinic antagonists; neuroleptics; vanilloid receptor agonists or antagonists; beta-adrenergics; corticosteroids; Serotonin (5-HT) receptor agonists or antagonists such as a $5\text{-HT}_{1B/1D}$, $5\text{-HT}_{2A}$, and $5\text{-HT}_3$ receptor antagonists; cholinergic (nicotinic) analgesics; cannabinoids; metabotropic glutamate subtype 1 receptor (mGluR1) antagonists; serotonin reuptake inhibitors such as sertraline; noradrenaline (norepinephrine) reuptake inhibitors such as reboxetine, in particular (S,S)-reboxetine; dual serotonin-noradrenaline reuptake inhibitors such as duloxetine; inducible nitric oxide synthase (iNOS) inhibitors such as S-[2-[(1-iminoethyl)-amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, and guanidinoethyldisulfide; acetylcholinesterase inhibitors; prostaglandin $E_2$ subtype 4 (EP4) antagonists such as N-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(1S)-1-({[5-chloro-2-(3-fluorophenoxy)pyridin-3-yl]carbonyl}amino)ethyl]benzoic acid; leukotriene B4 antagonists such as 1-(3-biphenyl-4-ylmethyl-4-hydroxychroman-7-yl)-cyclopentanecarboxylic acid; 5-lipoxygenase inhibitors; and sodium channel blockers.

Combinations with compounds or salts of the present invention also include analgesics such as acetominophen, naproxen sodium, ibuprofen, tramadol, trazodone; cyclobenzaprine; aspirin, celecoxib, valdecoxib, indomethacin, and other NSAIDs; antidepressants such as tricyclic antidepressants and selective serotonin reuptake inhibitors, for example antidepressants such as amitriptyline, imipramine, nortriptyline, doxepin, fluoxetine, sertraline, and paroxetine; muscle relaxants such as cyclobenzaprine; sleeping aids such as zolpidem.

Combinations with compounds or salts of the present invention also include analgesics such as acetominophen, naproxen sodium, ibuprofen, tramadol, aspirin, celecoxib, valdecoxib, indomethacin, and other NSAIDs; disease-modifying antirheumatic drugs (DMARDs) such as sulfasalazine or methotrexate; corticosteroids; and tumor necrosis factor (TNF) blockers such as etanercept and infliximab.

Combinations with compounds or salts of the present invention include topical corticosteroids; vitamin D analogs such as calcipotriene; anthralin; topical retinoids (i.e., vitamin A derivatives) such as acitretin and tazarotene; clobetasol propionate; methotrexate; azathioprine; cyclosporine; hydroxyurea; and immune-modulating drugs such as alefacept, efalizumab, and etanercept. Treatment with phototherapy, including psoralen ultraviolet A (psoralen UVA or PUVA) therapy, narrow-band ultraviolet B (UVB) therapy, and combination light therapy could be used with compounds or salts of the present invention and the aforementioned combinations.

Combinations with compounds or salts of the present invention include NSAIDs such as acetominophen, naproxen sodium, ibuprofen, tramadol, aspirin, celecoxib, valdecoxib, and indomethacin; and corticosteroids such as prednisone.

Combinations with compounds or salts of the present invention include analgesics such as acetominophen, naproxen sodium, ibuprofen, tramadol, aspirin, celecoxib, valdecoxib, indomethacin, and other NSAIDs; anti-inflammatory drugs; sulfasalazine, mesalamine, balsalazide, and olsalazine; corticosteroids; prednisone; budesonide; immunosuppressant drugs such as azathioprine, mercaptopurine, TNF blockers such as infliximab and adalimumab, methotrexate, and cyclosporine; antibiotics such as metronidazole and ciprofloxacin; anti-diarrheals such as loperamide; laxatives; anticholinergic drugs; antidepressants such as tricyclic antidepressants and selective serotonin reuptake inhibitors, for example antidepressants such as amitriptyline, imipramine, nortriptyline, doxepin, fluoxetine, sertraline, and paroxetine; alosetron; and tegaserod.

Compounds or salts of the present invention could also be administered with a long acting beta agonist.

Suitable examples of other therapeutic agents which may be used in combination with the compounds or salts of the invention include 5-Lipoxygenase (5-LO) inhibitors or 5-lipoxygenase activating protein (FLAP) antagonists, leukotriene antagonists (LTRAs) including antagonists of $LTB_4$, $LTC_4$, $LTD_4$, and $LTE_4$, histamine receptor antagonists including H1 and H3 antagonists, $\alpha_1$- and $\alpha_2$-adrenoceptor agonist vasoconstrictor sympathomimetic agents for decongestant use, muscarinic M3 receptor antagonists or anticholinergic agents, PDE inhibitors, e.g. PDE3, PDE4 and PDE5 inhibitors, theophylline, sodium cromoglycate, COX inhibitors both non-selective and selective COX-1 or COX-2 inhibitors (NSAIDs), oral and inhaled glucocorticosteroids, monoclonal antibodies active against endogenous inflammatory entities, β2 agonists, including long-acting β2 agonists, adhesion molecule inhibitors including VLA-4 antagonists, Kinin-$B_1$- and $B_2$-receptor antagonists, Immunosuppressive agents, Inhibitors of matrix metalloproteases (MMPs), tachykinin $NK_1$, $NK_2$ and $NK_3$ receptor antagonists, elastase inhibitors, adenosine A2a receptor agonists, inhibitors of urokinase, compounds that act on dopamine receptors, e.g. D2 agonists, modulators of the NFκB pathway, e.g. IKK inhibitors, modulators of cytokine signalling pathways such as syk kinase, or JAK kinase inhibitors, agents that can be classed as mucolytics or anti-tussive, and antibiotics.

According to the present invention, compounds or salts of the invention can be combined with:

H3 antagonists, Muscarinic M3 receptor antagonists, PDE4 inhibitors, glucocorticosteroids, adenosine A2a receptor agonists, β2 agonists, modulators of cytokine signalling pathways such as syk kinase, or, leukotriene antagonists (LTRAs) including antagonists of $LTB_4$, $LTC_4$, $LTD_4$, and $LTE_4$.

According to the present invention, compounds or salts of the invention can also be combined with: glucocorticosteroids, such as inhaled glucocorticosteroids with reduced systemic side effects, including prednisone, prednisolone, flunisolide, triamcinolone acetonide, beclomethasone dipropionate, budesonide, fluticasone propionate, ciclesonide, and mometasone furoate and mometasone furoate monohydrate; muscarinic M3 receptor antagonists or anticholinergic agents including in particular ipratropium salts, such as ipratropium bromide, tiotropium salts, such as tiotropium bromide, oxitropium salts, such as oxitropium bromide, perenzepine, and telenzepine, or β2 agonists, such as long-acting β2 agonists, including salmeterol, formoterol, QAB-149 and CHF-4226.

F. USE IN THE PREPARATION OF A COMPOSITION OR MEDICAMENT

In one embodiment, the present invention comprises methods for the preparation of a composition or medicament comprising the compounds or salts of the present invention for use in treating condition mediated by glucocorticoid receptor activity.

In another embodiment, the invention comprises the use of one or more compounds or salts of the present invention in the preparation of a composition or a medicament for inflammation, inflammation related condition, rheumatoid arthritis, dermatitis, Alzheimer's disease.

The present invention also includes the use of one or more compounds or salts of the present invention for preparation of a composition or a medicament for treating one or more conditions detailed in the Methods section.

G. SCHEMES

The compounds of the present invention may be prepared using the methods illustrated in the general synthetic schemes and experimental procedures detailed below. The reactions of the synthetic methods herein are carried out in suitable solvents which may be readily selected by one skilled in the art of organic synthesis, said suitable solvents generally being any solvent which is substantially nonreactive with the starting materials (reactants), the intermediates, or products at the temperatures at which the reactions are carried out. A given reaction may be carried out in one solvent or a mixture of more than one solvent. Depending on the particular reaction step, suitable solvents for a particular reaction step may be selected.

Preparation of compounds of the invention can involve the protection and deprotection of various chemical groups. The need for protection and deprotection, and the selection of appropriate protecting groups can be readily determined by one skilled in the art. The chemistry of protecting groups can be found, for example, in T. W. Greene and P. G. M. Wuts, *Protective Groups in Organic Synthesis,* 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high performance liquid chromatography (HPLC) or thin layer chromatography.

The starting materials used herein are either commercially available or may be prepared by routine synthetic methods.

The general synthetic schemes are presented for purposes of illustration and are not intended to be limiting.

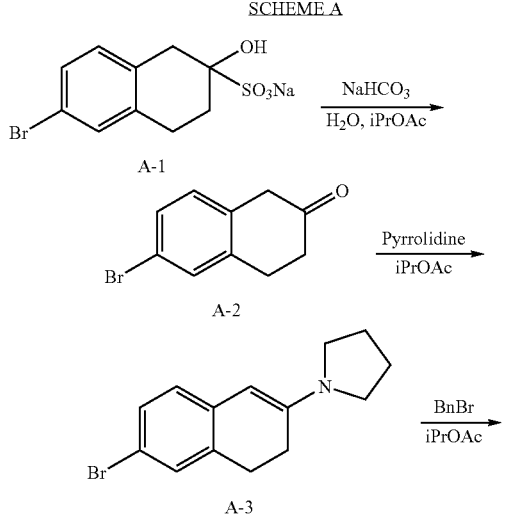

-continued
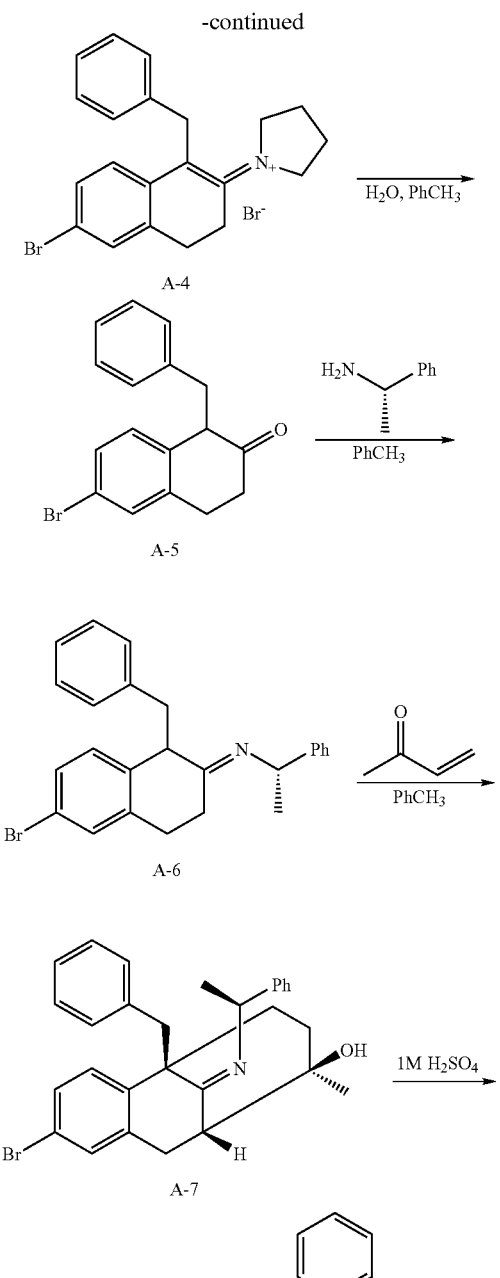
SCHEME B
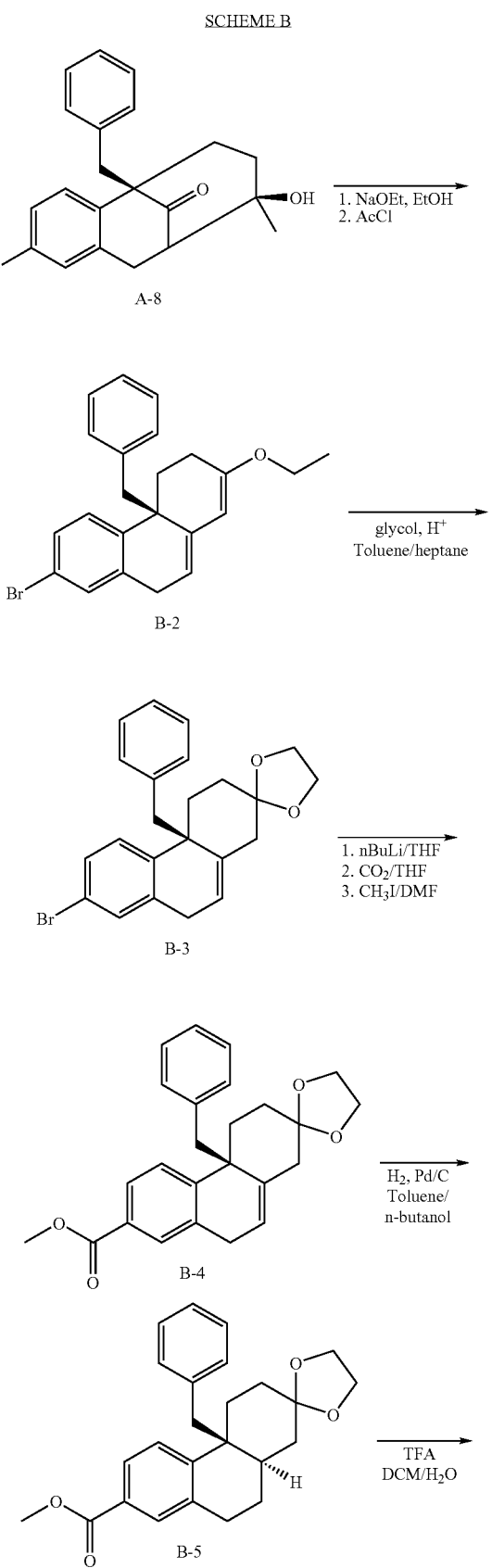
The 1(R)-Benzyl-5-bromo-9(S)-hydro-10(R)-hydroxy-10(R)-methyl-tricyclo[7.3.1.0$^{2,7}$]trideca-2,4,6-trien-13-one of Formula A-8 was prepared using the protocol described in Scheme A, which is generally disclosed in WO 00/66522. Ph depicts Phenyl. Bn depicts Benzyl. Compound A-1 can be purchased (for example, VOUS and Riverside; CAS No. 4133-35-1). Compound A-2 can be prepared as described in Org. Syn. 1971, 51, 109-112.

-continued
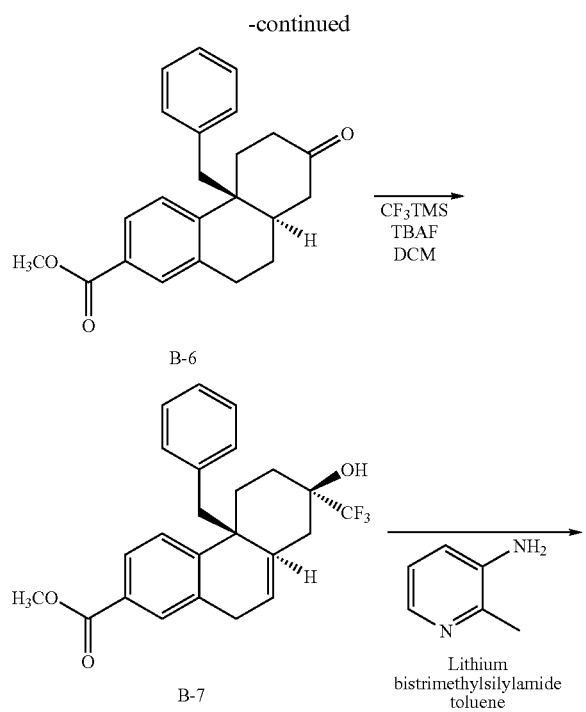
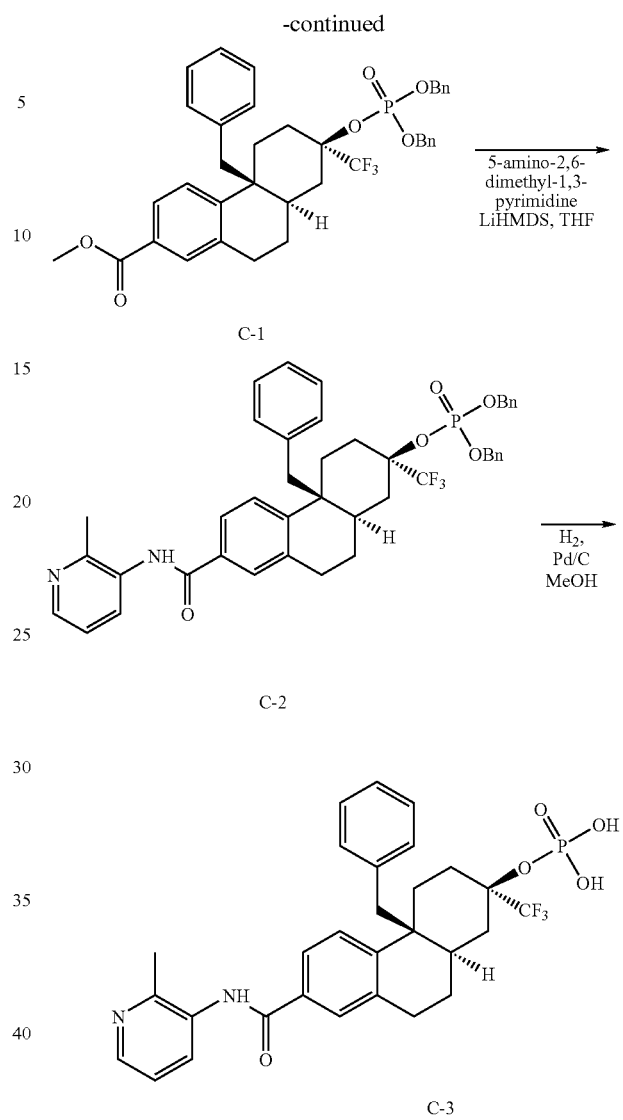
The (4βS,7R,8αR)-4β-benzyl-7-hydroxy-N-(2-methylpyridin-3-yl)-7-(trifluoromethyl)-4b,5,6,7,8,8α,9,10-octahydrophenanthrene-2-carboxamide was prepared as described in Scheme B.
The (2R,4αS,10αR)-4α-benzyl-7-((2-methylpyridin-3-yl)carbamoyl)-2-(trifluoromethyl)-1,2,3,4,4α,9,10,10α-octahydrophenanthren-2-yl dihydrogen phosphate of C-3 was prepared as described in Scheme C. Bn depicts benzyl.
SCHEME C
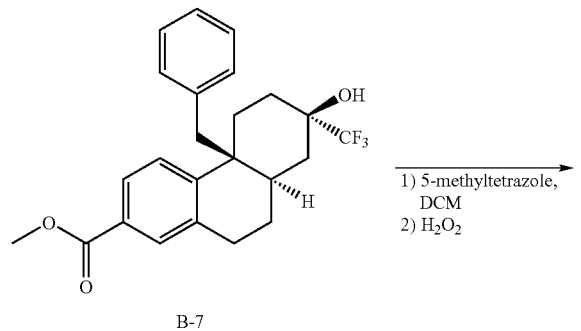
SCHEME D
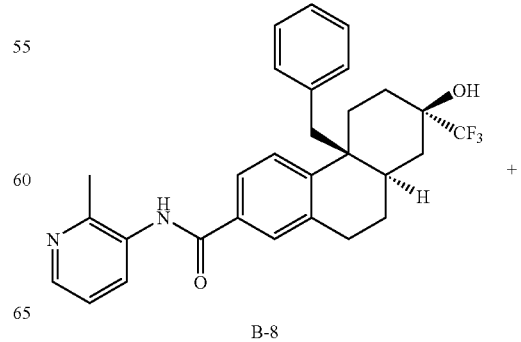

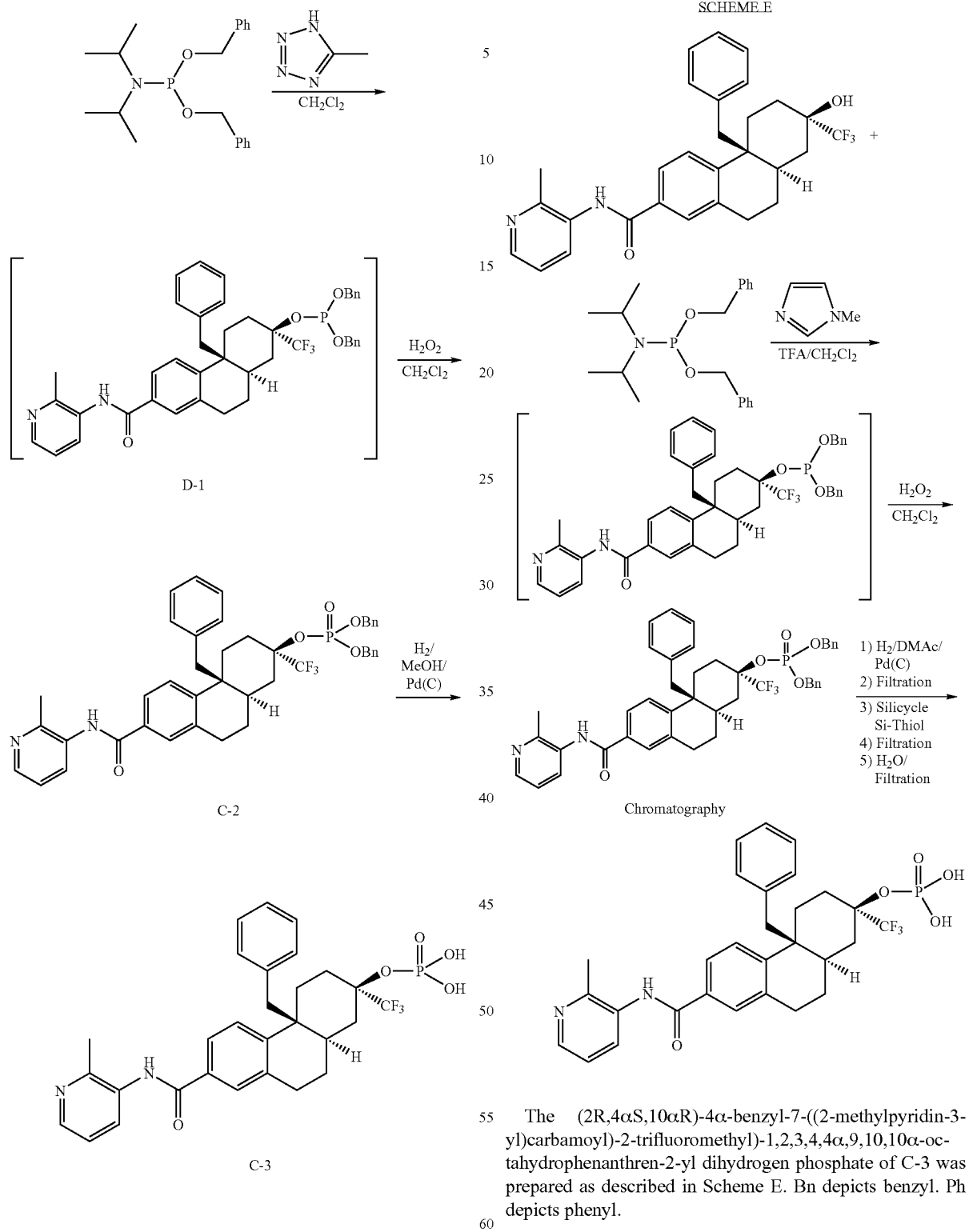

The (2R,4αS,10αR)-4α-benzyl-7-((2-methylpyridin-3-yl)carbamoyl)-2-(trifluoromethyl)-1,2,3,4,4α,9,10,10α-octahydrophenanthren-2-yl dihydrogen phosphate of C-3 was prepared as described in Scheme D. Bn depicts benzyl. Ph depicts phenyl.

The (2R,4αS,10αR)-4α-benzyl-7-((2-methylpyridin-3-yl)carbamoyl)-2-trifluoromethyl)-1,2,3,4,4α,9,10,10α-octahydrophenanthren-2-yl dihydrogen phosphate of C-3 was prepared as described in Scheme E. Bn depicts benzyl. Ph depicts phenyl.

H. PREPARATIONS AND EXAMPLES

Starting Material A-8 is 1(R)-Benzyl-5-bromo-9(S)-hydro-10(R)-hydroxy-10(R)-methyl-tricyclo[7.3.1.0$^{2,7}$]trideca-2,4,6-trien-13-one as depicted by the following formula:

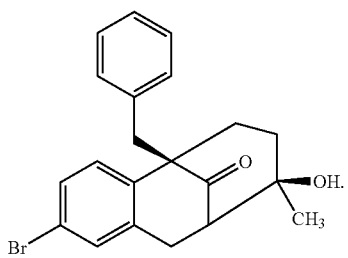

Preparation 1: (S)-4α-benzyl-7-bromo-2-ethoxy-3,4,4α,9-tetrahydrophenanthrene

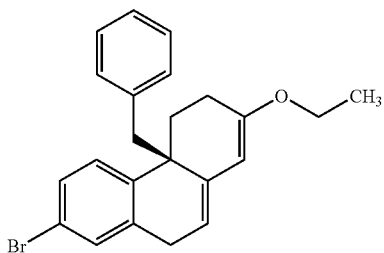

Starting Material A-8 (450 g; 1.17 moles) was dissolved in ethanol (4.5 L) at ambient temperature. 21% sodium ethoxide in ethanol (44 mL; 0.12 moles) was added and the mixture was heated to reflux for three hours. Once the Starting Material A-8 was consumed, the reaction mixture was chilled to −25° C. Acetyl chloride (250 mL; 3.51 moles) was slowly added to the mixture while the temperature was maintained near −25° C. After the addition was complete, the mixture was warmed to 0° C. and held there until the intermediate enone was consumed. The mixture was slurry at this point. 21% sodium ethoxide in ethanol (1.31 L; 3.51 moles) was added to the mixture while the temperature was maintained between −5° C. and 5° C. If the mixture was not basic, more sodium ethoxide was added. The temperature of the mixture was increased to 25° C. and then diluted with water (5.9 L). The mixture was filtered and the solid was washed with water (3×). The title compound (440 g; 85 area %) was obtained as a beige solid. $^1$H NMR (DMSO) δ ppm: 1.27 (t, 3H), 1.65 (dt, 1H), 2.06 (d, 1H), 2.21 (dd, 1H), 2.49 (m, 1H), 2.65 (m, 2H), 2.89 (m, 2H), 3.85 (q, 2H), 5.45 (m, 2H), 6.44 (d, 2H), 6.98 t, 2H), 7.06 (m, 2H), 7.25 (d, 1H), 7.33 (dd, 1H).

Preparation 2: (S)-4α-benzyl-7-bromo-2,2-(1,2-ethylenedioxy)-1,2,3,4,4α,9-hexahydrophenanthrene

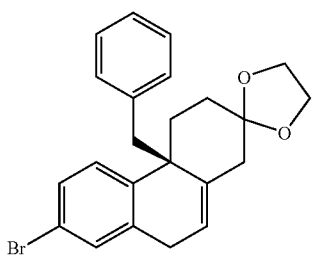

The (S)-4α-benzyl-7-bromo-2-ethoxy-3,4,4α,9-tetrahydrophenanthrene (1270 g; 3.2 moles; 85 area %, which may be prepared as described in Preparation 1) was dissolved in toluene (6.45 L). The ethylene glycol (898 mL; 16.1 moles) and p-toluenesulfonic acid (6.1 g; 0.03 moles) were added and the reaction heated to reflux. Solvent (1 L) was distilled from the mixture and replaced with fresh toluene (1 L). This distillation process was repeated twice more. More p-toluenesulfonic acid (6.1 g) was added each time fresh toluene was added. During the reaction, two intermediates (detected by LC) were formed as the substrate was converted into product. The end point of the reaction was an equilibrium point between the two intermediates and the product. Once the endpoint was reached, the mixture was cooled to ambient temperature. The mixture was washed with 0.5 M NaOH (2 L). The phases separated quickly and both were dark with a small rag layer. The mixture was washed with water (2 L). The phases separated very slowly. The mixture was dried by azeotropic distillation. Methanol (4 L) was added to the mixture and solvent (4 L) was distilled from the mixture. The methanol addition and solvent distillation were repeated twice more. Methanol was added to the mixture and precipitation occurred a few minutes later. More methanol (4 L) was added to the mixture and then brought to reflux. After 30 minutes, the mixture was cooled to 0° C. The mixture was filtered and the solid was washed with chilled methanol (2×2 L). The solid was dried in a vacuum oven at 65° C. The title compound (882 g; 98 area %) was obtained as a beige solid. $^1$H NMR (DMSO) δ ppm: 1.71 (m, 2H), 2.06 (m, 2H), 2.31 (dd, 1H), 2.39 (m, 1H), 2.68 (d, 1H), 2.77 (m, 1H), 2.86 (dd, 1H), 3.36 (d, 1H), 3.86 (m, 4H), 5.45 (m, 1H), 6.50 (m, 2H), 7.00 (m, 4H), 7.37 (dd, 1H), 7.44 (d, 1H).

Preparation 3: (S)-methyl 4β-benzyl-7,7-(1,2-ethylenedioxy)-4β,5,6,7,8,10-hexahydrophenanthrene-2-carboxylate

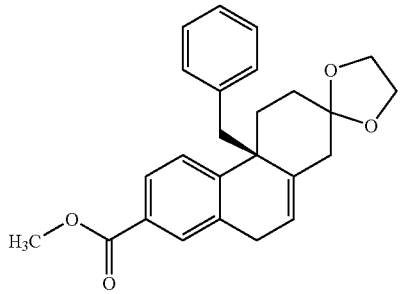

The (S)-4α-benzyl-7-bromo-2,2-(1,2-ethylenedioxy)-1,2,3,4,4α,9-hexahydrophenanthrene (719 g; 1.75 moles, which may be prepared as described in Preparation 2) was dissolved in tetrahydrofuran (7.19 L) and chilled to −70° C. The 1.6 M n-butyl lithium in hexane (2270 mL; 2.27 motes) was added at a rate such that the temperature was maintained below −60° C. The mixture held an additional 15 minutes after the addition. Carbon dioxide (108 g; 2.45 moles) was added while the temperature was maintained below −60° C. The mixture held an additional 15 minutes after the addition. The mixture was warmed to ambient temperature. Solvent (7 L) was distilled from the mixture at atmospheric pressure. DMF (7 L) was added to the mixture. The mixture was cooled to ambient temperature. Methyl iodide (152 mL; 2.45 moles) was added and the mixture was held until the reaction was completed (~1 hour). The mixture was heated to 70° C. and solvent was distilled by gradually reducing the pressure to 70 mmHg.

Once distillation had ceased, the mixture was cooled to room temperature. Water (6.5 L) was slowly added to the mixture to precipitate the product. The mixture was filtered and the solid washed with water (3×). The solid was dried on the filter. The crude product (736 g; 74 area %) was obtained as a beige solid. The product was purified by chromatography. 463 g of product was recovered from the chromatography. This material was separated from n-heptane (6130 mL). 394 g of the title compound was recovered. Another 70 g of title compound was recovered from the mother liquor by chromatography. $^1$H NMR (DMSO) δ ppm: 1.74 (m, 2H), 2.10 (m, 2H), 2.33 (dd, 1H), 2.45 (m, 1H), 2.72 (d, 1H), 2.79 (m, 1H), 2.94 (dd, 1H), 3.40 (d, 1H), 3.87 (m, 7H), 5.49 (m, 1H), 6.47 (m, 2H), 6.93 (m, 2H), 7.01 (m, 1H), 7.42 (d, 1H), 7.64 (d, 1H), 7.79 (dd, 1H).

Preparation 4: (4βS,8αR)-methyl 4β-benzyl-7,7-(1,2-ethylenedioxy)-4β,5,6,7,8,8α,9,10-octahydrophenanthrene-2-carboxylate

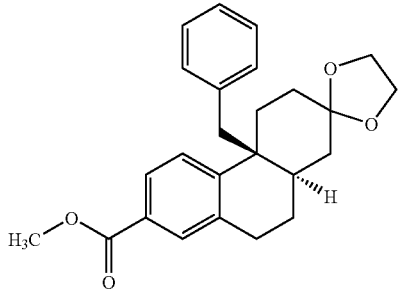

B-5

The (S)-methyl 4β-benzyl-7,7-(1,2-ethylenedioxy)-4β,5,6,7,8,10-hexahydrophenanthrene-2-carboxylate (201 g; 0.515 moles, which may be prepared as described in Preparation 3) and 50 ml of ethylene glycol was dissolved in toluene (2.0 L) in an autoclave. To this was added 10 grams of a 5% Pd/C (dry catalyst). The autoclave was then sealed and purged with nitrogen (three cycles) followed by hydrogen (three cycles). The reaction was run for 18 hours with a pressure of 80 psig and temperature of 50° C. HPLC analysis for completion and selectivity (typical selectivity's are: 95 to 5, Trans to Cis). The suspension was filtered through Celite® to remove the catalyst and the toluene solution is concentrated at 50° C., under vacuum, to approximately 200 ml. While still at 50° C., 1 L of 1-butanol was added and the solution heated to 60° C., until clear. Upon cooling, the resulting solid title compound was isolated by vacuum filtration (196 grams; 97%; Trans to Cis 95.75 to 4.24). $^1$H NMR (300 MHz, CDCl$_3$) δ ppm: 7.79 (bs, 1H, Ar—H), 7.47 (d, J=9 Hz, 1H, Ar—H), 7.13-7.05 (cm, 3H, Ar—H), 6.56-6.53 (cm, 2H, Ar—H), 6.43 (d, J=9 Hz, 1H, Ar—H), 4.04-3.93 (cm, 4H, 2-CH$_2$), 3.89 (s, 3H, CH$_3$), 3.08-3.03 (cm, 3H, CH$_2$, CH—H), 2.63 (d, J=15 Hz, CH—H), 2.22-1.72 (cm, 8H, 4-H$_2$), 1.57 (cm, 1H, CH—H); $^{13}$CNMR (CDCl$_3$, δ): 167.7, 149.2, 137.7, 136.4, 131.1, 130.5, 127.8, 127.7, 127.4, 126.3, 125.5, 108.9, 64.6, 64.5, 52.1, 40.5, 39.8, 38.3, 35.8, 31.6, 30.3, 27.9, 24.6.

Preparation 5: (4βS,8αR)-methyl 4β-benzyl-7-oxo-4β,5,6,7,8,8α,9,10-octahydrophenanthrene-2-carboxylate

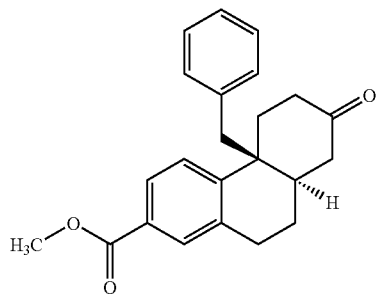

B-6

The (4βS,8αR)-methyl 4β-benzyl-7,7-(1,2-ethylenedioxy)-4β,5,6,7,8,8α,9,10-octahydrophenanthrene-2-carboxylate (150 g, 382 mmol, which may be prepared as described in Preparation 4) was dissolved in dichloromethane (630 ml). Water (270 ml) was added with stirring followed by trifluoroacetic acid (73 ml. 1150 mmol) via drop funnel over 30 minutes, maintaining the internal temperature below 30° C. After the addition was complete, the reaction was heated at 40° C. for 2 hours. In process check indicated incomplete reaction with around 9% (area percent) starting material. The layers were separated and fresh water (270 ml) and trifluoroacetic acid (31 ml) was added. The reaction mixture was heated at 40° C. for 1 hour. This process was continued until the starting material was consumed. The organic phase was washed with 5% aqueous sodium bicarbonate (300 ml), water (300 ml) and dried over MgSO$_4$ and concentrated to dryness to give 126.4 g of the title compound (representing a 95% yield). $^1$H NMR (DMSO) δ ppm: 7.70 (s, 1H), 7.37 (d, J=8.4 Hz, 1H), 7.11 (m, 3H), 6.6 (d, J=5.70 Hz, 2H), 6.45 (d, J=8.4 Hz, 1H), 3.80 (s, 3H), 3.80 (m, 2H), 3.04-1.48 (m, 11H).

Preparation 6: (4βS,7R,8αR)-methyl 4β-benzyl-7-hydroxy-7-(trifluoromethyl)-4β,5,6,7,8,8α,9,10-octahydrophenanthrene-2-carboxylate

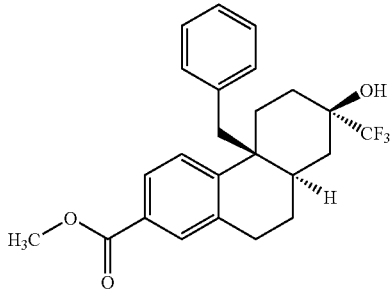

B-7

The (4βS,8αR)-methyl 4β-benzyl-7-oxo-4β,5,6,7,8,8α,9,10-octahydrophenanthrene-2-carboxylate (118 g, 0.339 mole, which may be prepared as described in Preparation 5) dissolved in dichloromethane was chilled to −50° C. The solution became turbid. 1.0 M Tetrabutylammonium fluoride a solution in THF (3.4 ml, 0.003 mol) was added with no appreciable temperature change. Trifluorotrimethylsilane (79 ml, 0.51 mol) was added over 20 minutes with a color change to bright orange to light red in color. The reaction mixture was held at −50° C. for about 2 hours and then allowed to warm to 0° C. Tetrabutylammonium fluoride (340 ml, 0.34 moles) was added very slowly at 0° C., to the reaction mixture over 45 minutes. An exotherm was observed with gas evolution. The reaction mixture was stirred 10 minutes and HPLC analysis indicated complete desilylialation. Water (1 L) was added to the reaction mixture and with vigorous stirring and allowed to warm to room temperature. The organic layer was washed with water (1 L). The organic layer was concentrated and chromatographed to produce 72 g, 51% of the title compound, with an additional 32 g of impure product. $^1$H NMR (DMSO) δ ppm: 7.70 (s, 1H), 7.37 (d, J=8.1 Hz, 1H), 7.09 (m, 3H), 6.5 (dd, J=1.2, 6.6 Hz, 2H), 6.38 (d, J=8.4 Hz, 1H), 3.80 (s, 3H), 3.80 (m, 2H), 3.09-1.21 (m, 13H).

Preparation 7: (4βS,7R,8αR)-methyl 4β-benzyl-7-(bis(benzyloxy)phosphoryloxy)-7-(trifluoromethyl)-4β,5,6,7,8,8α,9,10-octahydrophenanthrene-2-carboxylate

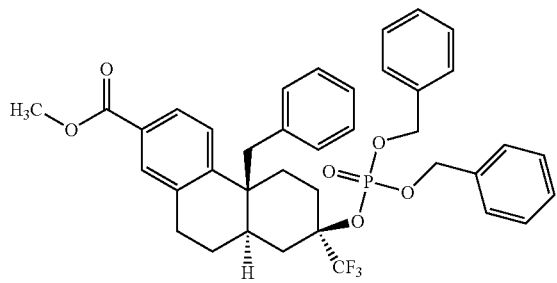

C-1

The (4βS,7R,8αR)-methyl 4β-benzyl-7-hydroxy-7-(trifluoromethyl)-4β,5,6,7,8,8α,9,10-octahydrophenanthrene-2-carboxylate (5.0 g; 11.9 mmol, which may be prepared as in Preparation 6) and 5-methyltetrazole (3.6 g; 43.0 mmol) were mixed together in dichloromethane (50 mL) at ambient temperature. Dibenzylphosphoramidite (8.3 mL; 25.1 mmol) was added and the mixture was stirred until the reaction was completed (1 hour). The mixture was chilled to 0° C. and 30% hydrogen peroxide (10 mL) was added. The reaction was stirred until the oxidation was completed (30 minutes). The aqueous phase was separated arom the organic phase. The organic phase was washed with 10% sodium meta-bisulfite (50 mL). The organic phase was dried with anhydrous magnesium sulfate and concentrated. The crude product was purified by silica gel chromatography with 15% ethyl acetate in hexanes. The purified title compound (8.41 g; 94% yield) was obtained as a colorless oil that contained 6% ethyl acetate by weight. $^1$H NMR (DMSO): δ 1.31 (t, 1H), 1.63-1.92 (m, 3H), 2.05-2.35 (m, 3H), 2.63 (d, 1H), 2.75-3.16 (m, 4H), 3.80 (s, 3H), 5.13 (m, 4H), 6.43 (d, 1H), 6.49 (m, 2H), 7.04-7.17 (m, 3H), 7.33-7.42 (m, 12H), 7.71 (d, 1H).

Preparation 8: dibenzyl (2R,4αS,10αR)-4α-benzyl-7-((2-methylpyridin-3-yl)carbamoyl)-2-(trifluoromethyl)-1,2,3,4,4α,9,10,10α-octahydrophenanthren-2-yl phosphate

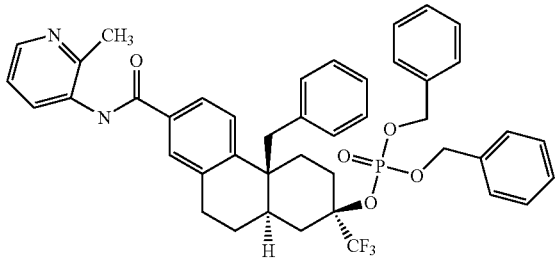

C-2

The (4βS,7R,8αR)-methyl 4β-benzyl-7-(bis(benzyloxy)phosphoryloxy)-7-(trifluoromethyl)-4β,5,6,7,8,8α,9,10-octahydrophenanthrene-2-carboxylate (7.9 g; 11.6 mmol, which may be prepared as in Preparation 7) and 3-amino-2 picoline (1.3 g; 12.2 mmol) were mixed together in tetrahydrofuran (80 mL) and chilled to 0° C. The 1 M solution of lithium bis trimethylsilyl)amide in tetrahydrofuran (24 mL; 24.4 mmol) was added while maintaining the temperature below 10° C. The mixture was stirred for 30 minutes. Water (50 mL) was added to the reaction mixture. The mixture was extracted with ethyl acetate. The organic extract was washed with water. The organic phase was dried with anhydrous magnesium sulfate and concentrated. The crude product was purified by silica gel chromatography with 70% ethyl acetate in hexanes. The purified title compound (6.79 g; 68% yield) was obtained as a yellow gum that contained 6% ethyl acetate by weight. $^1$H NMR (DMSO): δ 1.33 (t, 1H), 1.66-1.93 (m, 3H), 2.08-2.34 (m, 3H), 2.41 (s, 3H), 2.68 (d, 1H), 2.76-3.19 (m, 4H), 5.14 (m, 4H), 6.47 (d, 1H), 6.56 (m, 2H), 7.07-7.19 (m, 3H), 7.20-7.53 (m, 12H), 7.71 (d, 1H), 7.76 (s, 1H), 8.32 (d, 1H), 9.93 (s, 1H).

Example 1

(4βS,7R,8αR)-4β-benzyl-7-hydroxy-N-(2-methylpyridin-3-yl)-7-(trifluoromethyl)-4β,5,6,7,8,8α,9,10-octahydrophenanthrene-2-carboxamide

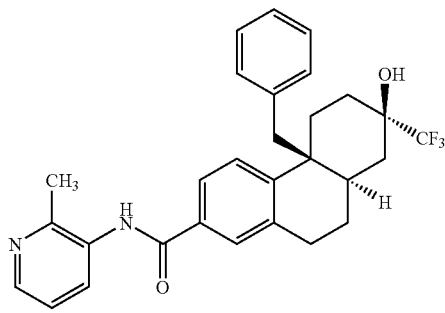

B-8

The (4βS,7R,8βR)-methyl 4α-benzyl-7-hydroxy-7-(trifluoromethyl)-4β,5,6,7,8,8α,9,10-octahydrophenanthrene-2-carboxylate (10 g; 23.9 mmol, which may be prepared as described in Preparation 6), and 3-amino-2-picoline (2.71 g;

25.1 mmol) were dissolved in toluene (200 mL). The 1M lithium bis(trimethylsilyl)amide in tetrahydrofuran (74.1 mL; 74.1 mmol) was added at a rate such that the temperature was maintained below 35° C. There was a mild exotherm and a solid precipitated during the addition. The mixture was held an additional 30 minutes after the addition. Water (250 mL) was added to the mixture. There was a mild exotherm and the solid dissolved. Ethyl acetate (50 mL) was added to the mixture to ensure the product did not precipitate. Stirring was stopped to allow the phases to separate. The aqueous phase was removed. The organic phase was washed with water (250 mL). Solvent (230 mL) was distilled at atmospheric pressure from the organic phase. The mixture was cooled to ambient temperature. The mixture was filtered and the solid was washed with toluene (2 times) followed by heptane (2 times). The solid was dried in a vacuum oven at 70° C. The title compound of the present example (10 g) was obtained as a beige solid. $^1$H NMR (DMSO) δ ppm: 1.32 (m, 1H), 1.82 (m, 4H), 2.10 (m, 4H), 2.41 (s, 3H), 2.8 (d, 1H), 3.08 (m, 3H), 6.00 (s, 1H), 6.43 (d, 1H), 6.59 (m, 2H), 7.12 (m, 3H), 7.25 (dd, 1H), 7.44 dd, 1H), 7.71 dd, 1H), 7.75 (d, 1H), 8.31 (dd, 1H), 9.91 (s, 1H).

Example 2

(2R,4αS,10αR)-4α-benzyl-7-((2-methylpyridin-3-yl)carbamoyl)-2-(trifluoromethyl)-1,2,3,4,4α,9,10,10α-octahydrophenanthren-2-yl dihydrogen phosphate

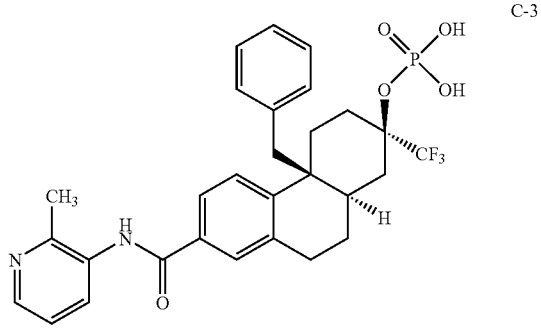

C-3

The dibenzyl (2R,4αS, 10αR)-4α-benzyl-7 (2-methylpyridin-3-yl carbamoyl)-2-(trifluoromethyl)-1,2,3,4,4α,9,10,10α-octahydrophenanthren-2-yl phosphate (6 g; 7.9 mmol, which may be prepared as described in Preparation 8) was dissolved in methanol (120 mL). 5% palladium on carbon (63% water) (1.3 g; 0.4 mmol) was added to the mixture. The mixture was treated with hydrogen (50 psi) at room temperature. The reaction stalled with 12% of the monobenzylic intermediate remaining. The mixture was filtered through a pad of Celite®. Fresh catalyst (1.3 g) was added to the solution and resubmitted to the hydrogenation conditions. Once the reaction was completed, the mixture was filtered through a pad of Celite®. The solution was concentrated to about 60 mL by distillation and not by using a rotary evaporator. During the distillation a white solid precipitated. The mixture was cooled to ambient temperature. The mixture was filtered and the solid washed with methanol. The solid was dried in a vacuum oven at 70° C. The compound of the present example (3.36 g; 75% yield) was obtained as a white solid and had an LC purity of 98 area %. $^1$H NMR (DMSO): δ 1.33 (t, 1H), 1.69-1.98 (m, 3H), 2.07-2.29 (m, 3H), 2.42 (s, 3H), 2.61-2.80 (m, 2H), 2.93-3.19 (m, 3H), 3.30 (d, 1H), 6.50 (d, 1H), 6.64 (m, 2H), 7.08-7.20 (m, 3H), 7.29 (dd, 1H), 7.48 (dd, 1H), 7.75 (dd, 2H), 8.33 (dd, 1H), 9.96, (s, 1H).

I. BIOLOGICAL DATA

For the following descriptions, the comparators are tricyclic compounds (see e.g., WO 2000/66522). The example and comparators compounds were prepared at Pfizer. Prednisolone was used as a clinically relevant comparator (P-6004; Sigma-Aldrich, St. Louis).

Comparator A is (4βS,7S,8αR)-4β-benzyl-7-hydroxy-N-((2-methylpyridin-3-yl)methyl)-7-(3,3,3-trifluoropropyl)-4β,5,6,7,8,8α,9,10-octahydrophenanthrene-2-carboxamide, having the following structure:

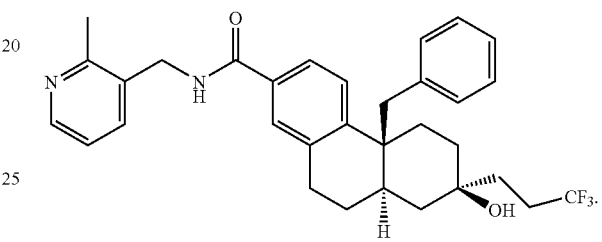

Comparator B is (4βS,7R,8αR)-4β-benzyl-N-(3,5-dimethylpyrazin-2-yl)-7-hydroxy-7-(trifluoromethyl)-4β,5,6,7,8,8α,9,10-octahydrophenanthrene-2-carboxamide, having the following structure:

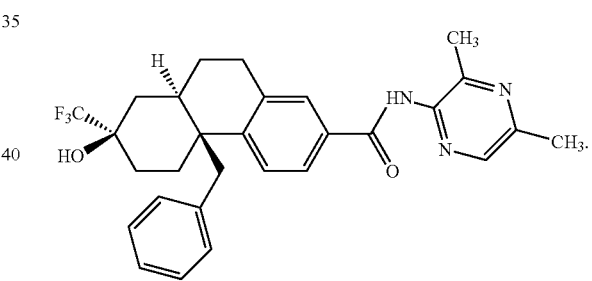

Comparator C is (4βS,7S,8αR)-4β-benzyl-7-hydroxy-N-(2-methylpyridin-3-yl)-7-(3,3,3-trifluoropropyl)-4β,5,6,7,8,8α,9,10-octahydrophenanthrene-2-carboxamide, having the following structure:

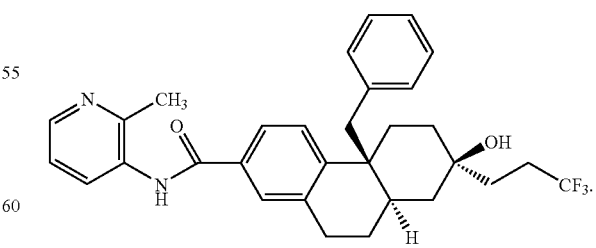

Comparator D is (4βS,7R,8αR)-4β-benzyl-7-hydroxy-N-(4-methylpyridin-3-yl)-7-(trifluoromethyl)-4β,5,5,7,8,8α,9,10-octahydrophenanthrene-2-carboxamide, having the following structure:

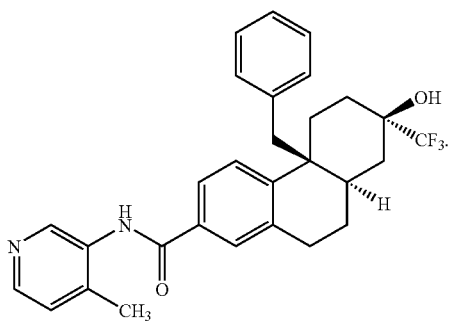

Comparator E is 4βS,7R,8αS)-4β-benzyl-7-hydroxy-N-(2-methylpyridin-3-yl)-10-oxo-7-(trifluoromethyl)-4β,5,6,7,8,8α,9,10-octahydrophenanthrene-2-carboxamide, having the following structure:

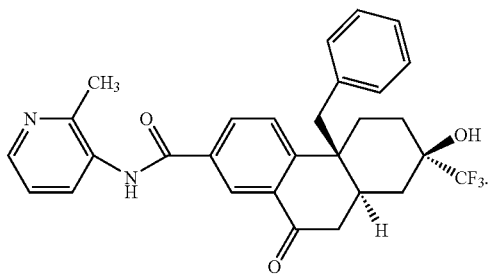

Comparator F is (4βS,7R,8αR,10R)-4β-benzyl-7,10-dihydroxy-N-(2-methylpyridin-3-yl)-7-(trifluoromethyl)-4β,5,6,7,8,8α,9,10-octahydrophenanthrene-2-carboxamide, having the following structure:

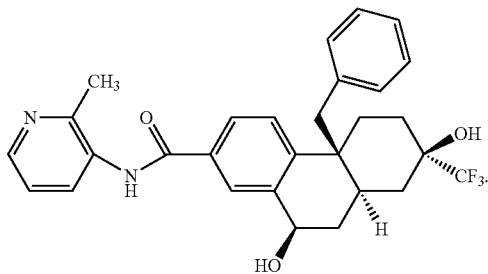

Comparator G is:

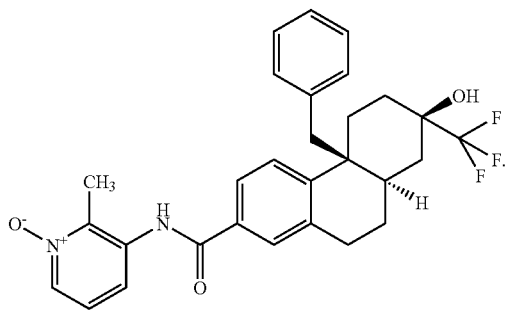

Comparator H is (4βS,7R,8αR)-4-benzyl-7-(difluoromethyl)-7-hydroxy-N-(2-methylpyridin-3-yl)-4β,5,6,7,8,8α,9,10 octahydrophenanthrene-2-carboxamide, having the following structure:

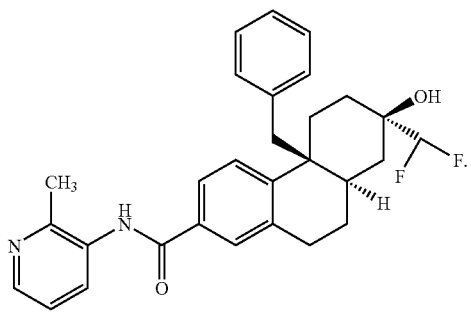

Comparator I is (4βS,7R,8αR)-4β-benzyl-7-hydroxy-N-(2-methylpyridin-3-yl)-7-(trifluoromethyl)-4β,5,6,7,8,8α-hexahydrophenanthrene-2-carboxamide, having the following structure:

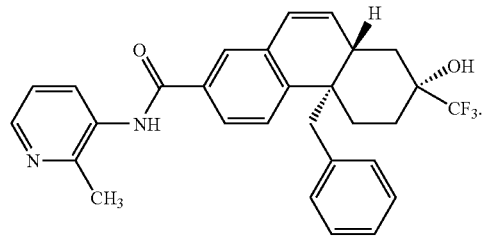

Comparator J is (4βS,7S,8αR)-4β-benzyl-N-2,4-dimethylpyrimidin-5-yl)-7-hydroxy-7-(3,3,3-trifluoropropyl)-4β,5,6,7,8,8α,9,10-octahydrophenanthrene-2-carboxamide, having the following structure:

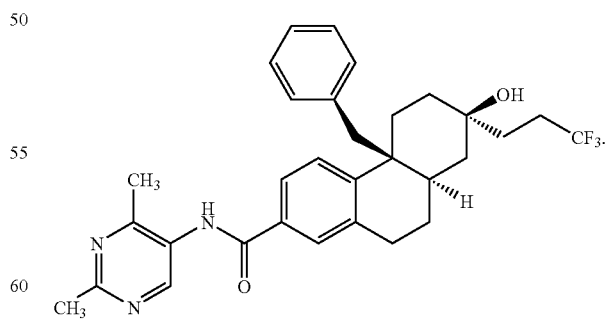

Comparator K is (2R,4αS,10αR)-4-benzyl-7-((2-methylpyridin-3-yl)carbamoyl)-2-(trifluoromethyl)-1,2,3,4,4α,9,10,10α-octahydrophenanthren-2-yl isobutyl carbonate, having the following structure:

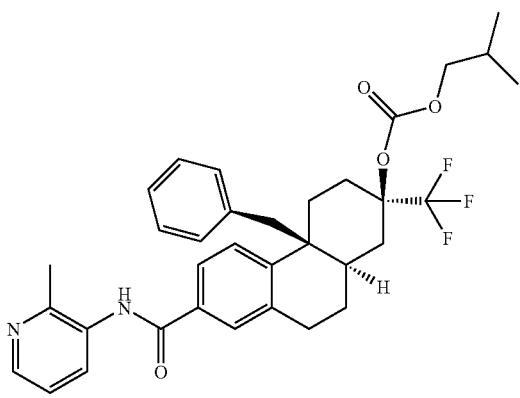

Conversion of Example 2 into Example 1

The Caco-2 cell monolayer is an in vitro tissue culture model of the intestinal epithelium. These cells are of human colonic origin and become polarized, fully differentiated enterocytes in 2-3 weeks. Once differentiated, these cells have tight junctions and express various biochemical processes such as active efflux transporters including P-glycoprotein (P-gp). With this model, it is possible to determine the apparent permeability ($P_{app}$) of a compound across the polarized Caco-2 cell monolayer.

An A→B Assay is performed with Caco-2 cell monolayers to determine compound $P_{app}$ from A chamber to B chamber. This $P_{app}$ is representative of luminal (gut) to serosal (blood) compound transport across intestinal epithelium that may be seen during intestinal absorption.

Example 2 did not significantly traverse a Caco-2 cell monolayer (A→B, $P_{app}=1.15e^{-6}$ cm/sec), whereas application of Example 2 to the apical compartment resulted in a significant elevation of Example 1 in both the apical and basolateral compartments. The data indicates a mechanism involving dephosphorylation of Example 2 to Example 1 via membrane-bound alkaline phosphatases located in the intestinal epithelia, followed by absorption of Example 1 across the Caco-2 cell monolayer (A→B, $P_{app}=37.5e^{-6}$ cm/sec).

Oral dosing of Example 2 (30 and 200 mg/kg) in portal vein-cannulated rats resulted in the detection of Example 1, but not Example 2, in portal vein plasma samples over a four-hour time period. These results indicated the occurrence of intestinal first-pass hydrolysis of Example 2 to Example 1 and selective intestinal absorption of Example 1.

Example 2 demonstrates enhanced solubility and intrinsic dissolution, which results in an improved oral absorption profile in rats via increased exposure (1.61 μg·hr/mL [vs. 0.46 μg·hr/mL for Example 1]) and $C_{max}$ (0.59 μg/mL [vs. 0.13 μg/mL for Example 1]), as well as decreased time to $C_{max}$ (0.8 hr [vs. 1.5 hr for Example 1]) in dogs. The bioavailability of Example 2 was improved compared with Example 1 in rats (F=59% for Example 2; F=17% for Example 1).

In Vitro Data

| Name | GRFP $IC_{50}$ (nM) | IL-6 $IC_{50}$ (nM) | IL-6 % Inhibition | TNFα $IC_{50}$ (nM) | TNFα % Inhibition |
|---|---|---|---|---|---|
| Example 1 HCL salt | 1.31 | .400 | 76.9 | 92.1 (28.8)[a] | 77.1 (62)[a] |
| Example 1 free base | | .360 | 86.1 | | |
| Example 2 | 79.0 (42)[a] | 60 (17)[a] | 60.2 (80)[a] | | |
| Comparator A | 7.10 | >36.4 | 59.9 | >1000 | 35 |
| Comparator B | 0.35 | 4 | 75.8 | | |
| Comparator C | 1.22 | 1.1 | 82.6 | | |
| Comparator D | 2.06 | 1.3 | 79.8 | | |
| Comparator E | 1.18 | 1.1 | 79.7 | | |
| Comparator F | 1.9 | 7 | 83.3 | | |
| Comparator G | 2.13 | 2.1 | 80.1 | | |
| Comparator H | 8.03 | 4.3 | 64.9 | | |
| Comparator I | 9.12 | 2.8 | 67.5 | | |
| Comparator J | 4.58 | 291 | 55 | | |
| Comparator K | 895 | | | | |
| Prednisolone | 0.526 | 4.2 (4.6)[a] | 102 (100)[a] | 14.9 (15.6)[a] | 100 |

[a] indicates additional results that were found.

GRFP: Glucocorticoid Receptor Binding

The glucocorticoid receptor fluorescence polarization ligand binding (GRFP) assay is used to evaluate direct binding of testing compounds to full-length glucocorticoid (GR) protein. Reagents for this assay are purchased from Invitrogen in a test kit. A fluorescent labeled GR ligand is used as a fluorescent tracer and test compounds compete with the fluorescent tracer for GR binding. The change in polarization value in the presence of test compounds is due to binding of test compounds to (GR) and is used to determine $IC_{50}$ and relative binding affinity of test compounds for GR.

IL-6 $IC_{50}$ and % Inhibition

Human A549 lung epithelial cells (American Type Culture Collection, Rockville, Md.) were cultured in Kaighn's F-12K medium with penicillin-streptomycin (10 U/mL) and 10% heat-inactivated fetal bovine serum (all from Invitrogen, Grand Island, N.Y.). A549 cells were plated at a density of 30,000 cells/well in 96-well plates and incubated overnight at 37° C. and with 5% $CO_2$. The cells were serum-starved by replacing the growth medium with serum-free Kaighn's F-12K medium with penicillin-streptomycin (10 U/mL) and, again, incubating overnight at 37° C. and with 5% $CO_2$. On the third day, the medium was replaced with fresh serum-free medium and the cells were incubated with or without compound (vehicle was DMSO at 0.1% maximum concentration) for approximately 1 hour and then stimulated with 1 ng/mL recombinant human IL-1β (R&D Systems, Minneapolis, Minn.) for 20 hours at 37° C. and with 5% $CO_2$. Cell supernatants were collected for determination of IL-6 levels using MSD (Meso Scale Discovery, Gaithersburg, Md.) 96-well Single Spot plates as per the manufacturer's instructions. Plates were read with an MSD Sector Imager 6000. Prednisolone (1 μM) was used as a maximal inhibitor and defined the 100% inhibition control. Vehicle was used to define the 0% inhibition control. Percent inhibition for each compound concentration, relative to these controls, was calculated using Excel (Microsoft, Redmond, Wash.). IC50 values were generated using GraFit 5.0 data analysis software (Erithacus Software Ltd., Surrey, UK).

TNFα $IC_{50}$ and % Inhibition

Human U937 pre-monocytic cells (American Type Culture Collection, Rockville, Md.) were cultured in RPMI 1640 with glutamine (2 mM), penicillin-streptomycin (10 U/mL) and 10% heat-inactivated fetal bovine serum (all from Invitrogen, Grand Island, N.Y.). Cells were differentiated to a monocyte/macrophage phenotype with phorbol 12-myristate 13-acetate (Sigma-Aldrich, St. Louis, Mo.), 20 ng/mL, overnight. The cells were then centrifuged, the medium aspirated, the cells resuspended in an equal volume of fresh RPMI 1640 medium with glutamine and penicillin-streptomycin and fetal bovine serum as listed above, and incubated for 48 hours at 37° C. and with 5% $CO_2$—Following recovery, the cells were scraped, counted, and plated in accordance to the experimental design prior to stimulation with LPS, as described below.

U937 cells were differentiated and plated at a density of 200,000 cells/well in 96-well plates. Cells were incubated with or without compound (vehicle was DMSO at 1% maximum concentration) for approximately one hour and then stimulated with 100 ng/mL lipopolysaccharide (LPS), E. coli serotype 0111:B4 (Sigma-Aldrich, St. Louis, Mo.) for four hours at 37° C. and with 5% $CO_2$. Cell supernatants were collected for determination of TNFα levels using an in-house sandwich-type ELISA. Mouse anti-human TNFα monoclonal antibody (clone 28401.111) and biotinylated goat anti-human TNFα (R&D Systems, Minneapolis, Minn.) were used as the capture and detection antibodies, respectively. Streptavidin-horseradish peroxidase (HRP) (R&D Systems, Minneapolis, Minn.) and K-Blue Substrate/Red Stop (Neogen, Lexington, Ky.) were used as the detection system. Absorbance was measured at 650 nm. TNFα concentrations were interpolated from a human TNFα recombinant protein (R&D Systems, Minneapolis, Minn.) standard curve using a four parameter logistics model by Magellan 4.11 data analysis software (Tecan, Durham, N.C.). Prednisolone (1 μM) was used as a maximal inhibitor and defined the 100% inhibition control. Vehicle was used to define the 0% inhibition control. Percent inhibition for each concentration of compound, relative to these controls, was calculated using Excel (Microsoft, Redmond, Wash.). IC50 values were generated using LabStats Fit Curve V4.R7.MO data analysis software (Pfizer Sandwich Laboratories, UK and Tessella Support Services plc, Abingdon UK).

Ex Vivo Human Whole Blood

This study compares the inhibition of IL-1β, IFNγ, IL-6, and TNFα production in ex vivo LPS-stimulated human whole blood by the glucocorticoid receptor (GR) ligands Comparator A, Example 1, and prednisolone.

Venous blood from human donors was collected as 10 ml aliquots in tubes containing sodium heparin (BD Vacutainer from Becton Dickinson and Company, Franklin Lakes, N.Y.). Blood was added to sterile polystyrene round bottom 96-well tissue culture plates (Corning Costar) at 100 μl/well, omitting the outside wells. Media (RPMI Medium 1640 with L-glutamine, Invitrogen Corporation, Carlsbad, Calif.) was added to the blood in 90 μl aliquots for a total volume of 190 μl. Outside wells were filled with 200 μl of media. Blood was placed in a humidified 37° C. incubator with 5% $CO_2$ while compounds were prepared (nearly 60 minutes).

Compounds were prepared from 10 mM stock solutions in dimethylsulfoxide (DMSO, Sigma-Aldrich). Stock compound was diluted serially 1/3 in DMSO (i.e. 5 μl compound+ 10 μl DMSO), followed by diluting each serial dilution 1/167 into vehicle solution (2% DMSO, 30% ethanol (AAPER Alcohol and Chemical Company), and 68% phosphate buffered saline (Dulbecco's Phosphate Buffered Saline without calcium chloride without magnesium chloride, Invitrogen Corporation, Carlsbad Calif.). Compound or vehicle was added to blood in 10 μl aliquots as triplicates. The final concentration of each prednisolone and Example 1 in the assay ranged from 100 nM to 0.457 nM. Comparator A concentrations ranged from 3000 nM to 1.4 nM. Final DMSO and ethanol concentrations in the assay were 0.1% and 1.5%. The samples were gently triturated twice to mix and replaced in the incubator. LPS stock (E. coli serotype 0111:B4, Sigma-Aldrich), stored in aliquots of 100 μg/ml in RPMI at −20° C., was diluted 1/50 in RPMI to make a working stock solution. After 60 minutes of incubation, 10 μl of the prepared LPS working stock was added to the blood to a final concentration of 100 ng/ml, omitting wells to be used as negative control. The samples were again gently triturated and the plates incubated overnight for 22 hours. Following incubation, the blood was centrifuged at 1500×g for 5 minutes and the plasma removed to either freeze at −20° C. or assay for cytokine release.

IL-1β, IFNγ, IL-6, and TNFα protein levels were measured using Meso Scale assay kits (Meso Scale Discovery, Gaithersburg, Md.). Reagents were allowed to come to room temperature. Meso Scale plates were blocked with 30 μl of human plasma/serum assay diluent with gentle shaking for 60 minutes at room temperature. Plates were washed 3× with wash buffer (PBS, Invitrogen Corporation, with 0.05% Tween-20, Sigma-Aldrich). Calibrators for standard curves were prepared in human plasma/serum assay diluent as a 115 serial dilution to achieve final concentrations ranging from 50000 pg/ml to 3.2 pg/ml. Samples and calibrators were added at 20 μl/well, then incubated at room temperature with gentle shaking for 90 minutes. Plates were again washed 3 times with wash buffer. Detection antibody was diluted in human plasma/serum antibody diluent to 1 μg/ml and added to the plate at 20 μl/well. Plates were incubated as before for 60 minutes and washed again. Read Buffer T<4×) was diluted 1:1 with mq$H_2O$ to 2 times concentration and 150 μl added to each well. Plates were analyzed on the SECTOR Imager 6000 (Meso Scale Discovery) to generate raw signal values.

IL-1β, IFN-γ, IL-6, and TNFα sample values were verified to be within the calibrator standard curves. Individual values were compared to positive and negative controls (vehicle treated blood with LPS and vehicle treated blood without LPS, respectively) to generate % inhibition. Triplicate values were averaged for each donor. The values for two donors were averaged (only one donor was used for IL-1β) and graphed using 4-parameter fit curves in the GraFit 5.0.11 application.

Mean Values of Prednisolone Inhibition

| Concentration (nM) | IFNγ (% inhibition) | TNFα (% inhibition) | IL-1β (% inhibition) | IL-6 (% inhibition) |
|---|---|---|---|---|
| 1000 | 99.95181 | 93.85394 | 94.92022 | 62.08045 |
| 333.3333 | 99.7687 | 88.98186 | 92.93646 | 40.25956 |
| 111.1111 | 94.99872 | 62.38366 | 73.1561 | 11.68419 |
| 37.03704 | 63.51763 | 27.66996 | 37.74411 | 5.032463 |
| 12.34568 | 25.733 | 12.86882 | 33.55115 | −0.41737 |
| 4.115226 | 5.164324 | 5.308603 | 20.98221 | −0.23188 |
| 1.371742 | 10.85844 | 6.613491 | 15.1055 | −0.94069 |
| 0.457247 | 4.925277 | 0.525846 | 9.64873 | 2.220454 |

Mean Values of Example 1 Inhibition

| Concentration (nM) | IFNγ (% inhibition) | TNFα (% inhibition) | IL-1β (% inhibition) | IL-6 (% inhibition) |
|---|---|---|---|---|
| 1000 | 78.72981 | 38.06288 | 53.51043 | 8.053268 |
| 333.3333 | 73.47381 | 36.04024 | 57.75726 | 2.1505 |
| 111.1111 | 60.63503 | 27.35287 | 39.67173 | 0.943985 |
| 37.03704 | 51.01941 | 18.68644 | 38.24203 | −0.82783 |
| 12.34568 | 26.70902 | 9.415215 | 21.54167 | −0.36893 |
| 4.115226 | −3.18296 | −1.31222 | 11.20262 | −1.06692 |
| 1.371742 | 19.77643 | 7.869405 | 22.38355 | 3.32595 |
| 0.457247 | 16.92723 | 8.956175 | 23.37486 | −1.36819 |

Mean Values of Comparator A Inhibition

| Concentration (nM) | IFNγ (% inhibition) | TNFα (% inhibition) | IL-1β (% inhibition) | IL-6 (% inhibition) |
|---|---|---|---|---|
| 3000 | 28.02163 | −3.03631 | 16.37219 | −1.97032 |
| 1000 | 16.52981 | −5.43701 | 14.96801 | −0.88954 |
| 333.3333 | −6.31952 | −4.61436 | 12.23526 | −2.8341 |
| 111.1111 | 8.737671 | −3.82374 | 8.59594 | −3.49518 |
| 37.03704 | −9.80677 | −4.19291 | 17.27236 | −3.52461 |
| 12.34568 | 0.016012 | 0.030908 | 22.84851 | −1.12581 |
| 4.115226 | −1.69672 | −0.86051 | 22.01534 | −4.3436 |
| 1.371742 | 18.09167 | 18.1316 | 31.97474 | 1.459164 |

In Vivo Data

Example 1 is a potent compound in disease models.

Mouse Collagen-Induced Arthritis (mCIA)

Mouse Collagen-induced arthritis is a commonly used chronic, preclinical model of rheumatoid arthritis in which joint swelling and bone destruction occur following immunization with type II collagen. Reduction of disease incidence and severity has been shown previously to be predictive of disease-modification and signs and symptoms mitigation, respectively, in a clinical setting.

In the traditional mCIA model, male DBA/J mice were immunized with 50 μg chick type II collagen (cCII) in complete Freund's adjuvant and then boosted 21 days later with 50 μg cCII in incomplete Freund's adjuvant. Treatment with compounds was initiated on the morning of the boost and continued for 56 days. The effectiveness of treatment was measured by disease incidence (i.e., number of mice showing any sign of disease) and disease severity, both of which were measured twice a week.

In the therapeutic mCIA model, induction of disease incidence and severity was synchronized via LPS stimulation. Male DBA/J mice were immunized with 100 ug of bovine type II collagen (bCII) on day 0. All mice received an intraperitoneal injection of 20 μg of LPS on day 28 and disease was allowed to develop through day 34. At day 34, all mice had disease (incidence=100%) with an average severity score of seven. Dosing of compounds was initiated in the therapeutic mode on day 34 and continued through day 49. Different treatments were compared by measuring the decrease in incidence (i.e., resolution of disease) and the decrease in severity of paw swelling over time.

Definition of mCIA Severity Scores (Maximal Score of 12/Mouse)

| Severity Score | Definition |
|---|---|
| 1 | Any redness or swelling of digits or paw |
| 2 | Gross swelling of the whole paw or deformity |
| 3 | Ankylosis of joints |

Example 1 had scores less than 2 for mCIA ($ED_{80}$) and less than 1 for mCIA ($ED_{50}$).

| Name | Therapeutic mCIA ($ED_{50}$ dose) | Therapeutic mCIA ($ED_{80}$ dose) | TNFα Suppression ($ED_{50}$ dose) | TNFα Suppression ($ED_{80}$ dose) | Osteocalcin Suppression ($ED_{50}$ dose) | Osteocalcin Suppression ($ED_{80}$ dose) |
|---|---|---|---|---|---|---|
| Example 1 free base | 0.4 | 1.5 | 0.46 | 1.82 | 2.91 | >10 |
| Comparator A | | | 60 | | 37 | |
| Comparator B | 2.9 | >10 | 1.64 | 2.91 | 2.39 | >10 |
| Comparator C | 2.0 | >10 | 0.27 | 1.33 | 1.01 | 2.84 |
| Comparator D | | | 1.47 | >20 | 1.18 | 3.06 |
| Comparator E | 0.5 | 2.6 | 0.14 | 1.18 | 0.17 | 1.71 |
| Comparator F | >10 | >10 | 2.11 | 5.67 | 1.19 | >10 |
| Comparator G | 0.6 | 3.0 | 2.90 | 3.33 | 1.12 | 7.27 |
| Comparator H | | | 0.23 | 0.72 | 0.51 | 1.46 |
| Comparator I | 17.0 | >20 | 0.73 | 5.45 | 5.20 | >20 |
| Comparator J | 3.0 | >20 | 0.09 | 0.79 | 0.73 | 3.58 |
| Prednisolone | 1.1 | 5.5 | 0.90 | 2.10 | 1.00 | 6.80 |

TNFα and Osteocalcin (OC) Suppression

The compounds were weighed and suspended in a vehicle of 0.5% methylcellulose/0.025% tween 20 (Sigma-Aldrich, St. Louis, Mo.). Compound suspensions were homogenized using a Polytron PT-3100 tissue homogenizer to create a very fine suspension and were then sonicated for 10 minutes using a water bath sonicator. Aliquots of each suspension were made for daily dosing at 0.2 ml/dose. Swiss Webster female mice, 10-12 weeks old, 28-29 grams, (Taconic, Germantown, N.Y.) were used in accordance with the guidelines of the Institutional Animal Care and Use Committee and in accordance with NIH guidelines on laboratory animal welfare. Mice were acclimated in the Pfizer animal facility for three to seven days prior to being utilized in a study. Prednisolone and compounds were administered by oral gavage for a total of 28 days. Each treatment group contained 5-10 mice. To establish a dosing regimen for the studies, a pilot pharmacodynamic time course experiment was conducted to quantify TNFα repression after a single $ED_{80}$ dose. Compounds which suppressed TNFα were dosed QD, while compounds which did not suppress TNFα>50% out to 24 h were dosed BID.

Body weights were measured on the first and last day of each experiment. Blood samples were obtained after three weeks of dosing for a steady-state pharmacokinetic (PK) analysis. To assess compound effects on LPS-induced TNFα, all mice received an intraperitoneal injection of LPS (*Salmonella typhosa*, L-7895; Sigma-Aldrich, St. Louis) 2.5 hr after the last dose on day 28. Mice were sacrificed 90 minutes after LPS administration. Serum samples were quantified for osteocalcin and TNFα using the multiplex assays (Linco Research, Inc, St. Charles, Mo.; Luminex 100, Austin, Tex.). Samples were diluted 1:20 and the assay was run according to manufacturer's instructions. The osteocalcin standard was purchased separately (Biomedical Technologies Inc., Stoughton, Mass.). Mice were fasted for 4 hours before serum was collected for TNFα, and osteocalcin levels. For each experiment, outliers were detected by calculating the number of standard deviations from the mean of the group. If the value being examined was more than 2.5 standard deviations from the mean, it was excluded from the rest of the calculations.

Percent inhibition values were then calculated for each mouse using the means of the vehicle and 10 mg/kg prednisolone control groups. The individual mouse percent inhibition values were fit to a four-parameter logistic model using the dose mean for each group. Since all four parameters were estimated and the lower plateau was not fixed at 0% and the upper plateau was not fixed at 100%, the $ED_{50}$ and $ED_{80}$ values were calculated by using an inverse calibration formula for a response equal to 50% or 80% inhibition or activation.

$ED_{50}$ and $ED_{80}$ values are the doses (in mg/kg) required to result in a 50% or 80% effect, respectively, on a particular endpoint. $ED_{50}$ and $ED_{80}$ values were obtained for the various endpoints using a four-parameter logistic fit. For compounds which were tested multiple times, $ED_{50}$ and $ED_{80}$ values were obtained using four-parameter logistic fits of the combined data from multiple experiments. For compounds which did not achieve an 80% effect, the $ED_{80}$ value is designated as >10 mg/kg or >20 mg/kg, depending on the highest dose tested.

House Dust Mite Model of Asthma

Mice were treated with three doses of Example 1 (0.1, 1 and 10 mg/kg, p.o., b.i.d.) or prednisolone (0.1, 1 and 10 mg/kg, p.o., b.i.d.). Separate groups of animals were treated with the respective vehicles, and no effect inflammatory cell influx into house dust mite-induced BAL inflammatory cell influx was demonstrated.

Example 1 mitigated cell infiltration into BAL fluid dose-dependently. Evaluation of BAL fluid cell types using flow cytometry showed significant reductions in eosinophils, neutrophils, lymphocytes and T-ells. In comparison, prednisolone conferred similar reductions in BAL fluid cell infiltration at similar doses (data not shown).

| Example 1 (mg/kg) | Total cells (% inhibition) | Eosinophils (% inhibition) | Neutrophils (% inhibition) | Lymphocytes (% inhibition) | T-cells (% inhibition) |
|---|---|---|---|---|---|
| 0.1 | 22 | 42 | 29 | 34 | 39 |
| 1 | 72 | 97 | 97 | 94 | 88 |
| 10 | 83 | 99 | 100 | 97 | 96 |

Dissociation Index

A dissociation index (DI) was chosen as a measurement to quantify the dissociation of compounds relative to that of prednisolone in terms of biomarkers of anti-inflammatory efficacy and side-effects. Dissociation indices were calculated using clinically relevant biomarkers that could be utilized in early clinical development. Serum osteocalcin and LPS-induced serum TNFα are accepted clinically as predictive for bone formation and anti-inflammatory efficacy, respectively.

The dissociation index was based on the following tenets:

1) Dissociation required a dose-margin between biomarkers of inflammation and side-effects and was defined by the formula:

$$DI = \frac{\text{Side-effect endpoint}}{\text{Anti-inflammatory endpoint}}$$

For example:

$$DI = \frac{\text{osteocalcin supprespression } (OC)\ ED_{50}\ (\text{or } EAUC_{50})}{\text{TNF}\alpha \text{ supprepression } (TNF\alpha)\ ED_{50}\ (\text{or } EAUC_{50})}.$$

2) The DI of a compound can be considered relative to that observed with prednisolone, its clinical comparator. The corrected or normalized DI was defined as compound DI divided by prednisolone DI.

Dissociation Index ($ED_{50}$ and $ED_{80}$)

| NAME | OC/TNFα ($ED_{50}$) | OC/TNFα ($ED_{80}$) |
|---|---|---|
| Example 1 free base | 6.33 | >5.49 |
| Comparator A | 0.62 | |
| Comparator B | 1.46 | >3.44 |

-continued

| NAME | OC/TNFα (ED$_{50}$) | OC/TNFα (ED$_{80}$) |
|---|---|---|
| Comparator C | 3.74 | 2.14 |
| Comparator D | 0.80 | <0.15 |
| Comparator E | 1.21 | 1.45 |
| Comparator F | 0.56 | >1.76 |
| Comparator G | 0.39 | 2.18 |
| Comparator H | 2.22 | 2.03 |
| Comparator I | 7.12 | >3.67 |
| Comparator J | 8.11 | 4.53 |
| Prednisolone | 1.11 | 3.24 |

Example 1, Comparator I, Comparator J had a DI greater than 5 for OC/TNFα (ED$_{50}$). Example 1 and Comparator J had a DI greater than 4 for OC/TNFα (ED$_{80}$).

Corrected Dissociation Index (ED$_{50}$ and ED$_{80}$) Based on Prednisolone

| Name | OC/TNFα (ED$_{50}$) | OC/TNFα (ED$_{80}$) |
|---|---|---|
| Example 1 free base | 5.70 | >1.69 |
| Comparator A | 0.56 | |
| Comparator B | 1.32 | >1.06 |
| Comparator C | 3.37 | 0.66 |
| Comparator D | 0.73 | <0.05 |
| Comparator E | 1.09 | 0.45 |
| Comparator F | 0.50 | >0.54 |
| Comparator G | 0.35 | 0.67 |
| Comparator H | 2.00 | 0.63 |
| Comparator I | 6.41 | >1.13 |
| Comparator J | 7.31 | 1.40 |

Example 1, Comparator I, Comparator J had a corrected DI greater than 5 for OC/TNFα (ED$_{50}$). Example 1 had a corrected DI greater than 1.50 for OC/TNFα (ED$_{80}$).

EAUC$_{50}$ and EAUC$_{80}$

Drug exposure, defined as drug plasma concentrations integrated over time (AUC), was used to make pharmacodynamic comparisons between prednisolone and Example 1. Due to the short half-lives of prednisolone and Example 1 in the mouse, AUC (0-4 hr) values accounted for more than 95% of the AUC (0-24 hr) values. Due to blood volume sampling limitations in mice, AUC (0-4 hr) values were used to make pharmacodynamic comparisons.

| | Prednisolone (AUC 0-4 hr) (μg * hr/mL) | | Example 1 (AUC 0-4 hr) (μg * hr/mL) | |
|---|---|---|---|---|
| | EAUC$_{50}$ | EAUC$_{80}$ | EAUC$_{50}$ | EAUC$_{80}$ |
| Serum TNFα | 0.81 | 0.95 | 0.22 | 0.33 |
| Serum osteocalcin | 0.56 | 1.60 | 1.30 | 4.20 |
| Cortical bone formation rate (BFR) | 0.09 | 0.60 | 0.27 | 1.55 |
| Disease incidence (traditional mCIA) | 0.25 | 0.60 | 0.04 | 0.10 |
| Disease severity (therapeutic mCIA) | 0.38 | 1.19 | 0.09 | 0.19 |
| Dissociation Index | | | | |
| OC/TNFα[a] | 0.7 | 1.7 | 5.9 | 12.7 |
| BFR/TNFα[a] | 0.1 | 0.6 | 1.2 | 4.7 |

-continued

| | Prednisolone (AUC 0-4 hr) (μg * hr/mL) | | Example 1 (AUC 0-4 hr) (μg * hr/mL) | |
|---|---|---|---|---|
| | EAUC$_{50}$ | EAUC$_{80}$ | EAUC$_{50}$ | EAUC$_{80}$ |
| BFR/disease incidence[b] | 0.4 | 1.0 | 6.8 | 15.5 |
| BFR/disease severity[b] | 0.2 | 0.5 | 3.0 | 8.2 |
| Corrected Dissociation Index | | | | |
| OC/TNFα[a] | | | 8.4 | 7.5 |
| BFR/TNFα[a] | | | 12.0 | 7.8 |
| BFR/disease incidence[b] | | | 17.0 | 15.5 |
| BFR/disease severity[b] | | | 15.0 | 16.4 |

[a]Data compared in mice in the same model.
[b]Data compared across mice in different models using plasma exposure to normalize. BFR, bone formation rate.

EAUC$_{50}$ and EAUC$_{80}$ Data Set 2

| | Example 1 | | Prednisolone | |
|---|---|---|---|---|
| Parameter | EAUC$_{50}$ | EAUC$_{80}$ | EAUC$_{50}$ | EAUC$_{80}$ |
| 28-day repeat dose model | | | | |
| Serum TNFα | 0.22 | 0.33 | 0.82 | 0.95 |
| Serum osteocalcin (OC) | 1.31 | 4.15 | 0.56 | 1.64 |
| Cortical bone formation rate (BFR) | 0.35 | 1.76 | 0.10 | 0.66 |
| Disease incidence (traditional mCIA) | — | 0.10 | — | 0.50 |
| Disease severity (therapeutic mCIA) | 0.09 | 0.19 | 0.38 | 1.19 |
| Disease incidence (therapeutic mCIA) | 0.12 | 0.33 | 0.68 | 1.38 |
| Corrected dissociation indices (DI) | | | | |
| OC/TNFα | 8.6 | 7.4 | | |
| BFR/TNFα | 16.0 | 7.6 | | |
| BFR/disease incidence | 14.5 | 10.6 | | |
| BFR/disease severity | 13.0 | 15.5 | | |

Example 1 is a dissociated compound. Example 1 had a DI and a corrected DI for EAUC$_{50}$ and EAUC$_{80}$ greater than 7 for OC/TNFα, BFR/TNFα, BFR/disease incidence, and BFR/disease severity.

Cortical Bone Histomorphometry to Determine BFR

During the in-life portion of each study, mice received two intraperitoneal (i.p.) injections (20 mg/kg, 100 ml/mouse) of calcein (C-0875; Sigma-Aldrich, St. Louis, Mo.) on days 1 and 26 for bone histomorphometry measurements. Calcein incorporates into the bone mineral and allows measurement of bone formation rate. Calcein was dissolved in 2% sodium bicarbonate. During the tissue harvest, the left tibiae were excised and cleaned for cortical histomorphometry measurements. After all skin and muscle were removed, tibiae were placed in 70% ethanol 4° C.) in the dark for a minimum of 24 hours.

Ground transverse sections were used for histomorphometric analysis of cortical bone. Bones were sectioned using a low-speed saw (Isomet, Buehler, Lake Bluff, Ill.) equipped with a diamond wafer blade. The end of each tibia was removed proximal to tibia-fibula synostosis and a 75 mm cross-section was cut. Using a roughened glass plate and a cork, sections were ground to ~25 mm until transparent and all labels were distinguishable under a fluorescent microscope. Sections were dehydrated using the following solutions for a minimum of two minutes each: 1) 70% ethanol, 2) 95% ethanol, 3) 100% ethanol, 4) 50/50 ethanol/xylene, and 5) xylene (twice) (#534056; Sigma-Aldrich, St. Louis, Mo.). Sections were mounted using Eukitt Quick Mounting Medium (#03989, Sigma-Aldrich, St. Louis, Mo.) after which coverslip was applied. Using the Osteomeasure Bone Analysis Program (Osteometrics, Inc., Decatur, Ga.), bone formation rate was calculated by tracing the $1^{st}$ and $3^{rd}$ fluorescent labels and the inner and outer perimeter of the bone. Bone formation rate was calculated by the following equation: (Inter-label width/Label interval)*(Labeled perimeter/Bone perimeter). At least five samples were measured from each treatment group in each study.

We claim:

1. A method of palliative or restorative treatment of a condition mediated by glucocorticoid receptor activity wherein the condition is an inflammation related condition, transplant rejection, or multiple sclerosis in a subject in need of such treatment, comprising administering to the subject a compound of Formula I:

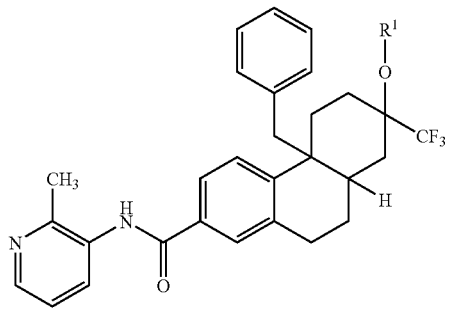

(I)

wherein $R^1$ is —P(O)(OH)$_2$;
or salt thereof.

2. The method of claim 1, wherein the condition is an inflammation related condition.

3. The method of claim 1, wherein the condition is asthma, dermatitis, inflammatory bowel disease, transplant rejection, multiple sclerosis, chronic uveitis, or chronic obstructive pulmonary disease.

4. The method of claim 1, wherein the condition is rheumatoid arthritis.

5. The method of claim 1, wherein the condition is dermatitis.

6. The method of claim 1, wherein the condition is asthma.

7. The method of claim 1, wherein the condition is inflammatory bowel disease.

8. A method of mitigating bone loss associated with prednisolone treatment, comprising administering a compound of Formula I:

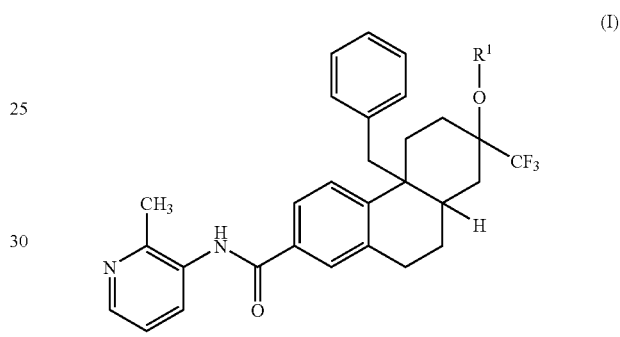

(I)

wherein $R^1$ is —P(O)(OH)$_2$;
or salt thereof, to a subject in need of prednisolone treatment.

* * * * *